United States Patent [19]

Leone et al.

[11] 4,031,127

[45] June 21, 1977

[54] ACYL HYDRAZINO THIOUREA DERIVATIVES AS PHOTOGRAPHIC NUCLEATING AGENTS

[75] Inventors: Ronald E. Leone; Wayne W. Weber, II; Donald P. Wrathall, all of Rochester, N.Y.

[73] Assignee: Eastman Kodak Company, Rochester, N.Y.

[22] Filed: June 29, 1976

[21] Appl. No.: 700,982

Related U.S. Application Data

[63] Continuation of Ser. No. 601,888, Aug. 6, 1975, abandoned.

[52] U.S. Cl. .............................. 260/465 D; 96/64; 260/552 R
[51] Int. Cl.² .............. C07C 121/52; C07C 121/60; C07C 157/09; G03C 5/30
[58] Field of Search ................... 260/552 R, 465 D; 96/64

[56] References Cited

UNITED STATES PATENTS

| | | | |
|---|---|---|---|
| 2,498,418 | 2/1950 | Hanford | 260/552 R X |
| 2,563,785 | 8/1951 | Ives | 96/64 |
| 2,588,982 | 3/1952 | Ives | 96/64 |
| 3,227,552 | 1/1966 | Whitmore | 96/64 X |
| 3,495,982 | 2/1970 | Blake | 96/64 |

FOREIGN PATENTS OR APPLICATIONS

| | | | |
|---|---|---|---|
| 1,269,640 | 4/1972 | United Kingdom | 96/64 |
| 1,250,151 | 1/1972 | United Kingdom | 96/64 |

*Primary Examiner*—Daniel E. Wyman
*Assistant Examiner*—Thomas A. Waltz
*Attorney, Agent, or Firm*—Carl O. Thomas

[57] ABSTRACT

Photographic nucleating agents are disclosed of the formula

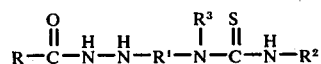

wherein
R is a hydrogen, phenyl, alkylphenyl, cyanophenyl, halophenyl, alkoxyphenyl, alkyl, cycloalkyl, haloalkyl, alkoxyalkyl or phenylalkyl substituent;
$R^1$ is a phenylene or alkyl, halo- or alkoxy substituted phenylene group;
$R^2$ is an alkyl, haloalkyl, alkoxyalkyl or phenylalkyl substituent having up to 18 carbon atoms; a cycloalkyl substituent; phenyl or naphthyl; an alkylphenyl, cyanophenyl, halophenyl or alkoxyphenyl substituent or

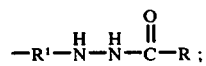

$R^3$ is hydrogen, benzyl, alkoxybenzyl, halobenzyl or alkylbenzyl;
the alkyl moieties, except as otherwise noted, in each instance include from 1 to 6 carbon atoms; and
the cycloalkyl moieties have from 3 to 10 carbon atoms.

45 Claims, No Drawings

ACYL HYDRAZINO THIOUREA DERIVATIVES AS PHOTOGRAPHIC NUCLEATING AGENTS

CROSS-REFERENCE TO RELATED APPLICATIONS

This application is a continuation-in-part of U.S. Ser. No. 601,888, filed Aug. 6, 1975, now abandoned.

The present invention is directed to novel photographic nucleating agents. More specifically this invention is directed to novel acylhydrazinophenylthioureas.

Photographic elements which produce images having an optical density directly related to the radiation received on exposure are said to be negative working. A positive photographic image can be formed by producing a negative photographic image and then forming a second photographic image which is a negative of the first negative—that is, a positive image. The advantage of forming a positive photographic image directly has long been appreciated in the art. A direct-positive image is understood in photography to be a positive image that is formed without first forming a negative image.

A conventional approach to forming direct-positive images is to use photographic elements employing internal latent image forming silver halide grains. After imagewise exposure, the silver halide grains are developed with a surface developer—that is, one that will leave the latent image sites within the silver halide grains substantially unrevealed. Simultaneously, either by uniform light exposure or by the use of a nucleating agent, the silver halide grains are subjected to development conditions that would cause fogging of a negative-working photographic element. The internal latent image forming silver halide grains which received actinic radiation during imagewise exposure develop under these conditions at a comparatively slow rate as compared to the internal image forming silver halide grains not exposed. The result is a direct-positive silver image. In color photography a corresponding dye image is typically produced. Multi-color direct-positive photographic images based on the above-described "internal image reversal" process have been investigated extensively in connection with image-transfer photography.

The term "nucleating agent" is employed herein in its art recognized usage to mean a fogging agent capable of permitting the selective development of internal image forming of silver halide grains which have not been image-wise exposed, in preference to the development of silver halide grains having an internal latent image formed by imagewise exposure. Nucleating agents are fogging agents which perform essentially the same function achieved by uniform light exposure during development in internal imae reversal processes.

Substituted hydrazines have been extensively investigated as nucleating agents for forming direct-positive photographic images with internal latent image emulsions. Illustrative patents directed to the use of hydrazines in forming direct-positive photographic images are Ives U.S. Pat. Nos. 2,563,785 and 2,588,982, issued Aug. 7, 1951 and Mar. 11, 1952, respectively; Whitmore U.S. Pat. No. 3,227,552, issued Jan. 4, 1966; and Knott and Williams British Pat. No. 1,269,640, published Apr. 6, 1972. Ives as well as Knott and Williams teach the incorporation of their nucleating agents in photographic developers. The nucleating agents of Whitmore can be incorporated directly within a photographic element or in an image-receiving element as well as in the photographic developer. Whitmore teaches the use of substituted hydrazine nucleating agents in image-transfer type photographic elements.

In considering the formation of direct-positive photographic images using conventional substituted hydrazine nucleating agents of the type disclosed above by Ives, Whitmore and Knott et al., a number of disadvantages have been identified. One disadvantage has stemmed from the tendency of incorporated hydrazine derivatives when used in conventional large quantities to liberate nitrogen gas in the course of nucleating silver halide. The liberated gas can result in bubbles being trapped within the binder for the photographic element. The bubbles can produce optical distortions or even cause discontinuities in one or more layers of the photographic element, thereby degrading the photographic image.

Another disadvantage of conventional substituted, hydrazine nucleating agents has been their temperature dependence. Specifically, photographic speeds have been noted to drop as processing temperatures increase. While processing temperatures can be controlled precisely in many photographic applications, this can be inconvenient in many instances and impossible in others, such as image-transfer photography, where processing frequently occurs at approximately the ambient temperature of the scene being photographed.

Another approach toward finding useful nucleating agents has been to synthesize heterocyclic nitrogen quaternary salts, such as disclosed by Kurtz and Harbison U.S. Pat. No. 3,734,738, issued May 22, 1973, and Kurtz and Heseltine U.S. Pat. No. 3,719,494, issued Mar. 6, 1973. Similarly, Lincoln and Heseltine U.S. Pat. Nos. 3,615,615 and 3,759,901, issued Apr. 13, 1970 and Sept. 18, 1973, teach the use of novel N-hydrazonoalkyl substituted heterocyclic nitrogen quaternary salts as nucleating agents. While these heterocyclic nucleating agents have reduced the concentrations required somewhat, they have generally shared the disadvantages of substituted hydrazine nucleating agents. Further, these quaternary salts can be disadvantageous in absorbing light within the visible spectrum.

This invention has as its purpose to provide photographic compositions and elements which are less temperature dependent. Specifically, this invention provides photographic compositions and elements useful in forming direct-positive images and which show diminished speed loss and in some instances speed gain with increasing processing temperatures. This invention also has as its purpose obviating optical distortions due to nitrogen gas liberation in photographic compositions and elements. Additionally, this invention has as its purpose providing photographic compositions and elements with more effective nucleating agents. These more effective nucleating agents can be employed in lower concentrations than have heretofore been practiced in the art. Further, this invention provides photographic elements and compositions having nucleating agents directly incorporated therein rather than in a developer composition. These nucleating agents can be adsorbed to the surface of internal latent image-forming silver halide grains, but they do not adsorb visible light. This invention further provides an advantage in allowing combinations of nucleating agents to be employed to control the speed of direct-positive silver halide compositions and elements.

In one aspect this invention is directed to a compound of the formula

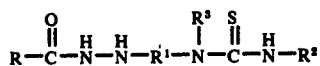

wherein R is a hydrogen, phenyl, alkyphenyl, cyanophenyl, halophenyl, alkoxyphenyl, alkyl, cycloalkyl, haloalkyl, alkoxyalkyl or phenylalkyl substituent; $R^1$ is phenylene or alkyl, halo- or alkoxy substituted phenylene group; $R^2$ is an alkyl, haloalkyl, alkoxyalkyl or phenylalkyl substituent having up to 18 carbon atoms; a cycloalkyl substituent; phenyl or naphthyl; an alkylphenyl, cyanophenyl, halophenyl or alkoxyphenyl substituent or

$R^3$ is hydrogen, benzyl, alkoxybenzyl, halobenzyl or alkylbenzyl; the alkyl moieties, except as otherwise noted, in each instance include from 1 to 6 carbon atoms; and the cycloalkyl moieties have from 3 to 10 carbon atoms.

Photographic compositions and elements employing acylhydrazinophenylthiourea nucleating agents are disclosed and claimed in our commonly assigned, concurrently filed patent application Ser. No. 701,050, titled PHOTOGRAPHIC COMPOSITIONS AND ELEMENTS INCLUDING INTERNAL LATENT IMAGE SILVER HALIDE GRAINS AND NUCLEATING AGENTS THEREFOR.

In concurrently filed, commonly assigned patent application Ser. No. 700,981, titled NUCLEATING AGENTS, RADIATION-SENSITIVE COMPOSITIONS AND PHOTOGRAPHIC ELEMENTS, compounds containing acylhydrazino-substituted rhodanine nuclei are disclosed to be useful as nucleating agents. These compounds are noted to decrease photographic speeds as processing temperatures increase similarly as conventional hydrazide nucleating agents.

Our invention can be better appreciated by reference to the following detailed description.

We have discovered that superior direct-positive image-forming photographic compositions and elements can be produced by employing an acylhydrazinophenylthiourea nucleating agent in combination with internal latent image silver halide grains.

These preferred, novel acylhydrazinophenylthioureas can be represented by the following formula:

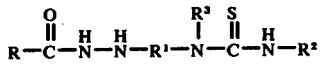

wherein
R is a hydrogen, phenyl, alkylphenyl, cyanophenyl, halophenyl, alkoxyphenyl, alkyl, cycloalkyl, haloalkyl, alkoxyalkyl or phenylalkyl substituent;

$R^1$ is a phenylene or alkyl, or halo- or alkoxy-substituted phenylene group;

$R^2$ is an alkyl, haloalkyl, alkoxyalkyl or phenylalkyl substituent having up to 18 carbon atoms; a cycloalkyl substituent; phenyl or naphthyl; an alkylphenyl, cyanophenyl, halophenyl or alkoxyphenyl substituent or

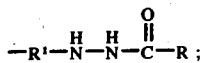

$R^3$ is hydrogen, benzyl, alkoxybenzyl, halobenzyl, or alkylbenzyl;
the alkyl moieties, except as otherwise noted, in each instance include from 1 to 6 carbon atoms; and
the cycloalkyl moieties have from 3 to 10 carbon atoms.

From formula I it is apparent that in the acyl group of the acylhydrazinophenylthioureas R can be the residue of a carboxylic acid, such as one of the acyclic aliphatic carboxylic acids, including formic acid, acetic acid, propionic acid, butyric acid, higher homologues of these acids having up to about 7 carbon atoms and halogen, alkoxy, phenyl and equivalent substituted derivatives thereof. The carboxylic acid can alternatively be aromatic carboxylic acid, such as benzoic acid, including alkyl, alkoxy, cyano, halogen and equivalent substituted derivatives thereof. In a preferred form the acyl group is formed by an aliphatic carboxylic acid having from 1 to 5 carbon atoms in its unsubstituted form. Where the acyl group is derived from benzoic acid, it is preferred that the substituents to the benzene ring be located in the para- or 4 position. The alkyl moieties in the substituents to the carboxylic acids are contemplated to have from 1 to 6 carbon atoms, preferably from 1 to 4 carbon atoms. In addition to the above discussed aromatic and acyclic aliphatic carboxylic acids, it is recognized that the carboxylic acid be chosen so that R is a cyclic aliphatic group having from about 3 to 10 carbon atoms, such as cyclopropyl, cyclobutyl, cyclopentyl, cyclohexyl, methylcyclohexyl, cyclooctyl, cyclodecyl and bridged ring variations, such as bornyl and isobornyl groups. Cyclohexyl is a specifically preferred cycloalkyl substituent. The use of alkoxy, cyano, halogen and equivalent substituted cycloalkyl substituents is contemplated.

The $R^1$ group in formula I can be an ortho-, meta- or para-phenylene group or a substituted equivalent thereof. Alkoxy, alkyl and halo-substituted phenylene groups are specifically contemplated. Compounds wherein $R^1$ is a para-phenylene group have been found to be more effective as nucleating agents as compared to the meta- and ortho- isomeric forms. We specifically prefer $R^1$ to be a para-phenylene group or a para-phenylene group which is substituted in the 3 ring position (with respect to the thiourea moeity) with an alkoxy, alkyl or halo-substituent. Exemplary of preferred phenylene substituents are alkoxy substituents having from 1 to 6 carbon atoms, alkyl substituents having from 1 to 6 carbon atoms, fluoro-, chloro-, bromo- and iodo-substituents. $R^1$ groups having from 6 to 10 total carbon atoms are specifically preferred.

Referring again to formula I, it is apparent that $R^2$ can take a variety of forms. In one specifically contemplated form $R^2$ can be an alkyl group or a substituted alkyl group, such as a haloalkyl group, alkoxyalkyl group, phenylalkyl group, or equivalent group, having a total of up to 18, preferably up to 12, carbon atoms. Specifically, $R^2$ can take the form of a methyl, ethyl, propyl, butyl, pentyl, hexyl, heptyl, octyl, nonyl, decyl or higher homologue group having up to 18 total carbon atoms; a fluoro-, chloro-, bromo- or iodo-substituted derivative thereof; a methoxy, ethoxy, propoxy, butoxy, or higher homologue alkoxy substituted derivative thereof, wherein the total number of carbon atoms are necessarily at least two up to 18; and a phenyl substituted derivative thereof, wherein the total number of carbon atoms is necessarily at least 7, as in the case of benzyl, up to about 18.

In an alternative form $R^2$ can be an aromatic substituent, such as phenyl or naphthyl (i.e. 1-naphthyl or 2-naphthyl) or an equivalent aromatic group—e.g. 1-, 2- or 9-anthryl, etc. It is also contemplated that the aromatic substituent can in turn be substituted. For example, cyano, fluoro-, chloro-, bromo-, iodo-, alkyl groups having from 1 to 6 carbon atoms and alkoxy groups having from 1 to 6 carbon atoms are contemplated. Compounds according to this invention wherein $R^2$ is a cyanophenyl substituent are less effective as nucleating agents than where $R^2$ is a halophenyl, alkylphenyl or alkoxyphenyl substituent. As in the case of R, we prefer para or 4 ring position substituted phenyl groups for nucleating applications.

In addition to the acyclic aliphatic and aromatic forms of $R^2$ discussed above, it is also contemplated that $R^2$ can take the form of a cyclic aliphatic substituent, such as a cycloalkyl substituent having from 3 to 10 carbon atoms. The use of cyclopropyl, cyclobutyl, cyclopentyl, cyclohexyl, methylcyclohexyl, cyclooctyl, cyclodecyl and bridged ring variations, such as bornyl and isobornyl groups, is contemplated. Cyclohexyl is a preferred cycloalkyl substituent. The use of alkoxy, cyano, halogen and equivalent substituted derivatives of the cycloalkyl substituent is contemplated.

In one form $R^3$ represents an unsubstituted benzyl group or substituted equivalents thereof, such as alkyl, halo- or alkoxy-substituted benzyl groups. In the preferred form no more than 6 and, most preferably, no more than 4 carbon atoms are contributed by substituents to the benzyl group. Substituents to the benzyl group are preferably para-substituents. Specifically preferred benzyl substituents are formed by unsubstituted, 4-halo-substituted, 4-methoxy-substituted and 4-methyl-substituted benzyl groups. In another specifically preferred form $R^3$ represents hydrogen.

From Formula I it is apparent that in one preferred form the acylhydrazinophenylthioureas can be symmetrical compounds—that is, bis(acylhydrazinophenyl)thioureas. Such compounds can be prepared by the following procedure: Using as a known starting material 4-nitrophenylhydrazine, this compound can be reacted with a carboxylic acid or halide or anhydride thereof (e.g., benzoic anhydride, formic acid, acetic acid, hexanoyl chloride, etc.) containing the desired acyl residue for the acylhydrazinophenylthiourea. Where the carboxylic acid is a liquid it can be used as a solvent for the reaction and an excess of the carboxylic acid is employed. In any instance a mutual solvent, such as benzene or acetonitrile, can be employed. Upon heating to reflux the 4-nitrophenylhydrazide of the corresponding carboxylic acid precipitates from solution. The precipitate can then be dissolved in ethanol and reduced to the corresponding 1-acyl-2-(4-aminophenyl) hydrazine by hydrogenation at room temperature using a palladium catalyst. After evaporating the ethanol, the 1-acyl-2-(4-aminophenyl)hydrazine is dissolved in water along with bis-carboxymethyl)trithiocarbonate and the pH is adjusted with sodium carbonate to a level in excess of 8, such as in the range of from 8 to 10. The mixture is stirred and heated to a temperature of from 80° to 95° C and then chilld to obtain the bis-(acylhydrazinophenyl)thiourea as a precipitate.

Where it is desired to synthesize an unsymmetrical acylhydrazinophenylthiourea according to this invention, such as, for example, when $R^2$ is intended to present an alkyl or carbocyclic group including substituted derivatives, the procedure described above is employed through the formation of the desired 1-acyl-2-(4-aminophenyl)hydrazine. An isothiocyanate containing the desired alkyl or carbocyclic moiety is dissolved in acetonitrile or ethanol along with the 1-acyl-2-(4-aminophenyl)hydrazine and heated to reflux. The unsymmetrical acylhydrazinophenylthiourea either precipitates or is precipitated by the addition of water and can be removed by filtering.

In those instances where $R^3$ represents a benzyl substituent the 1-acyl-2-(4-aminophenyl)hydrazine is dissolved in ethanol, along with benzaldehyde or a desired substituted benzaldehyde and heated to reflux. A Schiff base forms as a precipitate which can be converted to the 1-acyl-2-(4-benzylaminophenyl)hydrazine by hydrogenation in the presence of a platinum catalyst. Formation of the acylhydrazinophenylthiourea can be completed by reacting the 1-acyl-2-(4-benzylaminophenyl)hydrazine with an isothiocyanate following the preparation of unsymmetrical acylhydrazinophenylthioureas set out above. In a variant form the isothiocyanate can take the form of a 1-acyl-2-(4-isothiocyanatophenyl)hydrazine prepared by reacting thiophosgene with the corresponding 1-acyl-2-(4-aminophenyl)-hydrazine dissolved in an inert solvent such as benzene.

Illustrative specific acylhydrazinophenylthioureas useful in the practice of this invention include those set forth below in Table I.

TABLE I

| | |
|---|---|
| NA- 1 | 1,3-Bis[4-(2-formylhydrazino)phenyl]-thiourea |
| NA- 2 | 1,3-Bis[4-(2-acetylhydrazino)phenyl]-thiourea |
| NA- 3 | 1,3-Bis[4-(2-trifluoroacetylhydrazino)-phenyl]thiourea |
| NA- 4 | 1,3-Bis[4-(2-butyrylhydrazino)phenyl]-thiourea |
| NA- 5 | 1,3-Bis[4-(2-hexanoylhydrazino)phenyl]-thiourea |
| NA- 6 | 1,3-Bis[4-(2-benzoylhydrazino)phenyl]-thiourea |
| NA- 7 | 1,3-Bis[4-(2-o-toluoylhydrazino)phenyl]-thiourea |
| NA- 8 | 1,3-Bis{4-[2-(2,4-dimethylbenzoyl)hydrazino]phenyl}thiourea |
| NA- 9 | 1,3-Bis{4-[2-(4-ethylbenzoyl)-hydrazino]phenyl}thiourea |
| NA-10 | 1,3-Bis[4-(2-α-naphthoylhydrazino)-phenyl]thiourea |
| NA-11 | 1-[4-(2-formylhydrazino)phenyl]-3-methylthiourea |
| NA-12 | 1-[4-(2-formylhydrazino)phenyl]-3-butyl-thiourea |
| NA-13 | 1-[4-(2-acetylhydrazino)phenyl]-3-ethyl-thiourea |
| NA-14 | 1-[4-(2-formylhydrazino)phenyl]-3-cyclo-hexylthiourea |
| NA-15 | 1-[4-(2-benzoylhydrazino)phenyl]-3-phenylthiourea |
| NA-16 | 1-[4-(2-formylhydrazino)phenyl]-3-phenylthiourea |
| NA-17 | 1-[4-(2-acetylhydrazino)phenyl]-2-phenylthiourea |
| NA-18 | 1-[4-(2-acetylhydrazino)phenyl]-3-β-naphthylthiourea |
| NA-19 | 1-[4-(2-formylhydrazino)phenyl]-3-benzylthiourea |
| NA-20 | 1-[4-(2-formylhydrazino)phenyl]-3-heptylthiourea |
| NA-21 | 1-[4-(2-formylhydrazino)phenyl-3-decyl-thiourea |
| NA-22 | 1-[4-(2-formylhydrazino)phenyl]-3-(4-cyanophenyl)thiourea |
| NA-23 | 1-[4-(2-formylhydrazino)phenyl]-3-(4-methoxyphenyl)thiourea |
| NA-24 | 1-[4-(2-formylhydrazino)-3-methoxy-phenyl]-3-phenylthiourea |

TABLE I-continued

| | |
|---|---|
| NA-25 | 1-[4-(2-formylhydrazino)-3-methoxyphenyl]-3-butylthiourea |
| NA-26 | 1-[4-(2-formylhydrazino)-3-methoxyphenyl]-3-cyclohexylthiourea |
| NA-27 | 1-[4-(2-formylhydrazino)-3-methoxyphenyl]-3-(4-methoxyphenyl)thiourea |
| NA-28 | 1-[4-(2-trifluoroacetylhydrazino)-phenyl]-3-phenylthiourea |
| NA-29 | 1-{4-[2-(4-cyanobenzoyl)hydrazino]-phenyl}-3-phenylthiourea |
| NA-30 | 1-{4-[2-(4-chlorobenzoyl)hydrazino]-phenyl}-3-phenylthiourea |
| NA-31 | 1-{4-[2-(4-chlorobenzoyl)hydrazino]-phenyl}-3-phenylthiourea |
| NA-32 | 1-{4-[2-(4-methylbenzoyl)hydrazino]-phenyl}-3-phenylthiourea |
| NA-33 | 1-{4-[2-(4-methoxybenzoyl)hydrazino]-phenyl}-3-phenylthiourea |
| NA-34 | 1-{4-[2-(4-chlorobenzoyl)hydrazino]-phenyl}-3-benzylthiourea |
| NA-35 | 1-{4-[2-(4-fluorobenzoyl)hydrazino]-phenyl}-3-benzylthiourea |
| NA-36 | 1-[3-(2-formylhydrazino)phenyl]-3-phenylthiourea |
| NA-37 | 1-[3-(2-formylhydrazino)phenyl]-3-(4-methoxyphenyl)thiourea |
| NA-38 | 1-[2-(2-formylhydrazino)phenyl]-3-phenylthiourea |
| NA-39 | 1-[4-(2-formylhydrazino)phenyl]-1-benzyl-3-phenylthiourea |
| NA-40 | 1-[4-(2-acetylhydrazino)phenyl]-1-benzyl-3-phenylthiourea |
| NA-41 | 1-[4-(2-benzoylhydrazino)phenyl]-1-(2-chlorobenzyl)-3-phenylthiourea |
| NA-42 | 1-[4-(2-acetylhydrazino)phenyl]-1-(4-methoxybenzyl)-3-phenylthiourea |
| NA-43 | 1-[4-(2-formylhydrazino)phenyl]-1-(4-methylbenzyl)-3-methylthiourea |
| NA-44 | 1-[4-(2-acetylhydrazino)phenyl]-1-benzyl-3-[4-(2-formylhydrazino)phenyl]-thiourea |

The acylhydrazinophenylthiourea nucleating agents can be employed with any conventional photographic element capable of forming a direct-positive image containing at least one radiation-sensitive layer containing silver halide grains capable of forming an internal latent image upon exposure to actinic radiation. As employed herein, the terms "internal latent image silver halide grains" and "silver halide grains capable of forming an internal latent image" are employed in the art-recognized sense of designating silver halide grains which produce substantially higher optical densities when coated, imagewise exposed and developed in an internal developer than when comparably coated, exposed and developed in a surface developer. Preferred internal latent image silver halide grains are those which when examined according to normal photographic testing technqiues, by coating a test portion on a photographic support at a density of from 3 to 4 grams/m², exposing to a light intensity scale (such as, for example, with a 500 watt tungsten lamp at a distance of 61 cm) for a fixed time between $1 \times 10^{-2}$ and 1 second and developing for 5 minutes at 25° C in Kodak Developer DK-50 (a surface developer) provide a density of at least 0.5 density units less than when this testing procedure is repeated substituting for the surface developer Kodak Developer DK-50 containing 0.5 gram per liter of potassium iodide (an internal developer). The internal latent image silver halide grains most preferred for use in the practice of this invention are those which when tested using an internal developer and a surface developer as indicated above produce an optical density with the internal developer at least 5 times that produced by the surface developer. It is additionally preferred that the internal latent image silver halide grains produce an optical density of less than 0.4 and, most preferably, less than 0.25 when coated, exposed and developed in surface developer as indicated above—that is, the silver halide grains are initially substantially unfogged and free of latent image on their surface.

The surface developer referred to herein as Kodak Developer DK-50 is described in the *Handbook of Chemistry and Physics*, 30th ed., 1947, Chemical Rubber Publishing Co., Cleveland, Ohio, p. 2558, and has the following composition:

| | |
|---|---|
| Water, about 125° F (52° C) | 500.0 cc |
| N-methyl-p-aminophenol sulfate | 2.5 g |
| Sodium sulfite, desiccated | 30.0 g |
| Hydroquinone | 2.5 g |
| Sodium metaborate | 10.0 g |
| Potassium bromide | 0.5 g |
| Water to make | 1.0 liter. |

Internal latent image silver halide grains which can be employed in the practice of this invention are well known in the art. Patents teaching the use of internal latent image silver halide grains in photographic emulsions and elements include Davey et al. U.S. Pat. No. 2,592,250, issued May 8, 1952; Porter et al. U.S. Pat. No. 3,206,313, issued Sept. 14, 1965; Milton U.S. Pat. No. 3,761,266, issued Sept. 25, 1973; Ridgway U.S. Pat. No. 3,586,505, issued June 22, 1971; Gilman et al. U.S. Pat. No. 3,772,030, issued Nov. 13, 1973; Gilman et al. U.S. Pat. No. 3,761,267, issued Sept. 25, 1973; and Evans U.S. Pat. No. 3,761,276, issued Sept. 25, 1973, the disclosures of which are here incorporated by reference.

The internal latent image silver halide grains preferably contain bromide as the predominant halide. The silver bromide grains can consist essentially of silver bromide or can contain silver bromoiodide, silver chlorobromide, silver chlorobromoiodide crystals and mixtures thereof. Internal latent image forming sites can be incorporated into the grains by either physical or chemical internal sensitization. Davel et al., cited above, for example, teaches the physical formation of internal latent image forming sites by the halide conversion technique. Chemical formation of internal latent image forming sites can be produced through the use of sulfur, gold, selenium, tellurium and/or reduction sensitizers of the type described, for example, in Sheppard et al. U.S. Pat. No. 1,623,499, issued Apr. 5, 1927; Waller et al. U.S. Pat. No. 2,399,083, issued Apr. 23, 1946; McVeigh U.S. Pat. No. 3,297,447, issued Jan. 10, 1967 and Dunn U.S. Pat. No. 3,297,446, issued Jan. 10, 1967, as taught in the patents cited in the preceding paragraph. Internal latent image sites can also be formed through the incorporation of metal dopants, particularly Group VIII platinum metals such as ruthenium, rhodium, palladium, iridium, osmium and platinum, as taught by Berriman U.S. Pat. No. 3,367,778, issued Feb. 6, 1968. The preferred foreign metal ions are polyvalent metal ions which include the above-noted Group VIII dopants as well as polyvalent metal ions such as lead, antimony, bismuth, arsenic and the like. In highly preferred embodiments, the silver halide grains are formed in the presence of bismuth, lead or iridium ions. In a preferred approach the internal latent image sites can be formed within the silver halide grains during precipitation of silver halide. In an alternate approach a core grain can be formed which is treated to form the internal latent image sites and then a shell deposited over the core grains, as taught by Porter et al., cited above.

The silver halide grains employed in the practice of this invention are preferably monodispersed, and in some embodiments are preferably large-grain emulsions made according to Wilgus, German OLS No. 2,107,118, published Sept. 2, 1971, which is incorporated herein by reference. The monodispersed emulsions are those which comprise silver halide grains having a substantially uniform diameter. Generally, in such emulsions, no more than about 5 percent, by weight, of the silver halide grains smaller than the mean grain size and/or no more than about 5 percent, by number, of the silver halide grains larger than the mean grain size vary in diameter from the mean grain diameter by more than about 40 percent. Preferred photographic emulsions of this invention comprise silver halide grains, at least 95 percent, by weight, of said grains having a diameter which is within 40 percent, preferably within about 30 percent, of the mean grain diameter. Mean grain diameter, i.e., average grain size, can be determined using conventional methods, e.g., such as projective area as shown in an article by Trivelli and Smith entitled "Empirical Relations between Sensitometric and Size-Frequency Characteristics in Photographic Emulsion Series" in *The Photographic Journal*, Vol. LXXIX, 1939, pp. 330-338. The aforementioned uniform size distribution of silver halide grains is a characteristic of the grains in monodispersed photographic silver halide emulsions. Silver halide grains having a narrow size distribution can be obtained by controlling the conditions at which the silver halide grains are prepared using a double-run procedure. In such a procedure, the silver halide grains are prepared by simultaneously running an aqueous solution of a silver salt, such as silver nitrate, and an aqueous solution of a water-soluble halide, for example, an alkali metal halide such as potassium bromide, into a rapidly agitated aqueous solution of a silver halide peptizer, preferably gelatin, a gelatin derivative or some protein peptizer. The pH and the pAg employed in this type of procedure are interrelated. For example, changing one while maintaining the other constant at a given temperature can change the size frequency distribution of the silver halide grains which are formed. However, generally the temperature is about 30° to about 90° C, the pH is up to about 9, preferably 4 or less, and the pAg is up to about 9.8. Suitable methods for preparing photographic silver halide emulsions having the required uniform particle size are disclosed in the article entitled "Ia: Properties of Photographic Emulsion Grains", by Klein and Moisar, *The Journal of Photographic Science*, Vol. 12, 1964, pp. 242-251; an article entitled "The Spectral Sensitization of Silver Bromide Emulsions on Different Crystallographic Faces", by Markocki, *The Journal of Photographic Science*, Vol. 13, 1965, pp. 85-89; an article entitled "Studies on Silver Bromide Sols, Part I. The Formation and Aging of Monodispersed Silver Bromide Sols", by Ottewill and Woodbridge, *The Journal of Photographic Science*, Vol. 13, 1965, pp. 98-103; and an article entitled "Studies on Silver Bromide Sols, Part II. The Effect of Additives on the Sol Particles", by Ottewill and Woodbridge, *The Journal of Photographic Science*, Vol. 13, 1965, pp. 104-107.

Where internal latent image sites have been formed through internal chemical sensitization or the use of metal dopants, the surface of the silver halide grains can be below that which will produce substantial density in a surface developer—that is, less than 0.4 when coated, exposed and surface developed as described above. The silver halide grains are preferably predominantly silver bromide grains chemically surface sensitized to a level which would provide a maximum density of at least 0.5 using undoped silver halide grains of the same size and halide composition when coated, exposed and developed as described above.

Surface chemical sensitization can be undertaken using techniques such as those disclosed by Sheppard, Waller et al., McVeigh or Dunn, cited above. The silver halide grains can also be surface sensitized with salts of the noble metals, such as ruthenium, palladium and platinum. Representative compounds are ammonium chloropalladate, potassium chloroplatinate and sodium chloropalladite, which are used for sensitizing in amounts below that which produces any substantial fog inhibition, as described in Smith and Trivelli U.S. Pat. No. 2,448,060, issued Aug. 31, 1948, and as antifoggants in higher amounts, as described in Trivelli and Smith U.S. Pat. Nos. 2,566,245 issued Aug. 28, 1951 and 2,566,263, issued Aug. 28, 1951. The silver halide grains can also be chemically sensitized with reducing agents, such as stannous salts (Carroll U.S. Pat. No. 2,487,850, issued Nov. 15, 1949), polyamines, such as diethylene triamine (Lowe et al. U.S. Pat. No. 2,518,698, issued Aug. 15, 1950), polyamines, such as spermine (Lowe et al. U.S. Pat. No. 2,521,925, issued Sept. 12, 1950), or bis($\beta$-aminoethyl)sulfide and its water-soluble salts (Lowe et al. U.S. Pat. No. 2,521,926, issued Sept. 12, 1950).

The internal latent image silver halide grains can be optically sensitized using conventional techniques. For instance, spectral sensitization can be obtained by treating the silver halide grains with a solution of a sensitizing dye in an organic solvent or the dye may be added in the form of a dispersion as described in Owens et al. British Pat. No. 1,154,781 published June 11, 1969.

Sensitizing dyes useful in sensitizing silver halide emulsions are described, for example, in Brooker et al. U.S. Pat. No. 2,526,632, issued Oct. 24, 1950; Sprague U.S. Pat. No. 2,503,776, issued Apr. 11, 1950; Brooker et al. U.S. Pat. No. 2,493,748, issued Jan. 10, 1950; and Taber et al. U.S. Pat. No. 3,384,486, issued May 21, 1968. Spectral sensitizers which can be used include the cyanines, merocyanines, complex (tri- or tetranuclear) cyanines, holopolar cyanines, styryls, hemicyanines (e.g., enamine hemicyanines) oxonols and hemioxonols.

Preferred optical sensitizers include cyanine and merocyanine dyes, such as those described in U.S. Pat. Nos. 1,846,301 and 1,846,302, both issued Feb. 23, 1932, and 1,942,854, issued Jan. 9, 1934, all by Brooker; 1,990,507 by White, issued Feb. 12, 1935; 2,112,140, issued Mar. 22, 1938; 2,165,338, issued July 11, 1939; 2,493,747, issued Jan. 10, 1950, and 2,739,964, issued Mar. 27, 1956, all by Brooker et al.; 2,493,748 by Brooker et al., issued Jan. 10, 1950; 2,503,776, cited above; and 2,519,001, issued Aug. 15, 1950, both by Sprague; 2,666,761 by Heseltine et al., issued Jan. 19, 1954; 2,734,900, by Heseltine, issued Feb. 14, 1956; and 2,739,149 by Van Lare issued Mar. 20, 1956; and Kodak Limited British Pat. No. 450,958 accepted July 15, 1936.

To obtain the benefits of this invention, the internal latent image silver halide grains and an acylhydrazinophenylthiourea nucleating agent are brought together in a radiation-sensitive layer of a photographic element. In a preferred form of the invention, the silver halide grains and the acylhydrazinophenylthiourea nucleating agent are incorporated in a radiation-sensitive silver halide emulsion of a type employed in photography. Techniques for forming photographic silver halide emulsions are generally well known to those skilled in the art. Techniques for forming and washing silver halide emulsions are generally taught in *Product Licensing Index*, Vol. 92, Dec. 1971, publication 9232, paragraphs I and II.

The photographic emulsions and elements described in the practice of this invention can contain various colloids alone or in combination as vehicles, as binding agents and as various layers. Suitable hydrophilic materials include both naturally occurring substances such as proteins, for example, gelatin, gelatin derivatives, cellulose derivatives, polysaccharides such as dextran, gum arabic and the like; and synthetic polymeric substances such as water-soluble polyvinyl compounds like poly(vinylpyrrolidone), acrylamide polymers and the like.

The described photographic emulsion layers and other layers of a photographic element employed in the practice of this invention can also contain, alone or in combination with hydrophilic, water-permeable colloids, other synthetic polymeric compounds such as dispersed vinyl compounds such as in latex form and particularly those which increase the dimensional stability of the photographic materials. Suitable synthetic polymers include those described, for example, in U.S. Pat. Nos. 3,142,568 by Nottorf, issued July 28, 1964; 3,193,386 by White, issued July 6, 1965; 3,062,674 by Houck et al., issued Nov. 6, 1962; 3,220,884 by Houck et al., issued Nov. 30, 1965; 3,287,289 by Ream et al., issued Nov. 22, 1966; and 3,411,911 by Dykstra, issued Nov. 19, 1968; particularly effective are those water-insoluble polymers or latex copolymers of alkyl acrylates and methacrylates, acrylic acid, sulfoalkyl acrylates or methacrylates, those which have cross-linking sites which facilitate hardening or curing, those having recurring sulfobetaine units as described in Canadian Pat. No. 774,054 by Dykstra, and those described in U.S. Pat. No. 3,488,708 by Smith, issued Jan. 6, 1970.

The photographic emulsion layers can contain a variety of conventional photographic addenda. For example, hardeners of the type disclosed in *Product Licensing Index*, cited above, paragraph VII, can be employed. Similarly plasticizers, lubricants and coating aids of the type disclosed in *Product Licensing Index*, cited above, paragraphs XI and XII, can be employed.

The acylhydrazinophenylthiourea nucleating agents of this invention can be employed in any desired concentration that will permit a degree of selectivity in developing imagewise silver halide grains capable of forming an internal latent image, which grains have not been imagewise exposed, as compared to silver halide grains containing an internal latent image formed by imagewise exposure.

In a preferred form of this invention the acylhydrazinophenylthiourea nucleating agents are adsorbed to the surface of the internal latent image silver halide grains and employed in concentrations ranging from 0.1 to 200 mg of adsorbed nucleating agent per mole of silver. Preferably 0.5 to 25 mg of adsorbed nucleating agent per mole of silver is employed and, most preferably, 1 to 15 mg of adsorbed nucleating agent per mole of silver. Optimum concentrations can, of course, vary somewhat from one application to another. Where the acylhydrazinophenylthiourea nucleating agent is to be adsorbed to the surface of the silver halide grains, it can be adsorbed using the procedures well known to those skilled in the art for adsorbing sensitizing dyes, such as cyanine and merocyanine dyes, to the surface of silver halide grains.

It is specifically contemplated to employ in combination with acylhydrazinophenylthiourea nucleating agents other conventional nucleating agents. In a specifically preferred form one or a combination of acylhydrazinophenylthiourea nucleating agents are employed at a concentration of up to about 200 mg per mole of silver, as indicated above, in combination with a conventional substituted hydrazine type nucleating agent which is present in a concentration of from about 200 mg to about 2 grams per mole of silver. Where the acylhydrazinophenylthiourea nucleating agent actually increases photographic speed, with increasing processing temperatures, using the nucleating agent in combination with a conventional nucleating agent which decreases photographic speed with increasing processing temperatures, can result in a surprising degree of temperature insensitivity for the speed and developability of the resulting photographic emulsion.

In one preferred form of this invention the acylhydrazinophenylthiourea nucleating agents are employed in combination with hydrazide and hydrazone nucleating agents of the type disclosed by Whitmore, cited above. Such hydrazides and hydrazones are nitrogen-containing compounds having the formulas

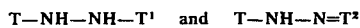

where T is an aryl radical and including substituted aryl radical; $T^1$ is an acyl or a sulfonyl radical; and $T^2$ is an alkylidene radical and including substituted alkylidene radicals. Typical alkyl radicals for the substituent T have the formula M-$T^3$— wherein $T^3$ is an aryl radical (such as phenyl, 1-naphthyl, 2-naphthyl, etc.) and M can be such substituents as hydrogen, hydroxy, amino, alkyl, alkylamino, arylamino, heterocyclic amino (amino containing a heterocyclic moiety), alkoxy, aryloxy, acyloxy, arylcarbonamido, alkylcarbonamido, heterocyclic carbonamido (carbonamido containing a heterocyclic moiety), arylsulfonamido, alkylsulfonamido, and heterocyclic sulfonamido (sulfonamido containing a heterocyclic moiety). Typical acyl and sulfonyl radicals for the substituent $T^1$ have the formula

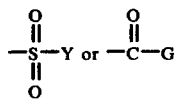

PS wherein Y can be such substituents as alkyl, aryl and heterocyclic radicals. G can represent a hydrogen atom or the same substituents as Y as well as radicals having the formula

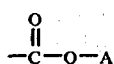

to form oxalyl radicals wherein A is an alkyl, aryl or a heterocyclic radical. Typical alkylidene radicals for the substituent $T^2$ have the formula =C—$D_2$ wherein D can be a hydrogen atom or such radicals as alkyl, aryl and heterocyclic radicals. Typical aryl substituents for the above-described hydrazides and hydrazones include phenyl, naphthyl, diphenyl, and the like. Typical heterocyclic substituents for the above-described hydrazides and hydrazones include azoles, azines, furan, thiophene, quinoline, pyrazole, and the like. Typical alkyl (or alkylene) substituents for the above-described hydrazides and hydrazones have 1 to 22 carbon atoms including methyl, ethyl, isopropyl, n-propyl, isobutyl, n-butyl, t-butyl, amyl, n-octyl, n-decyl, n-dodecyl, n-octadecyl, n-eicosyl, n-docosyl, etc.

Illustrative specific hydrazide (named as hydrazine derivatives) and hydrazone nucleating agents useful in the practice of this invention include those set forth below in Table II.

TABLE II

| H-1 | 1-acetyl-2-phenylhydrazine |
| H-2 | 1-acetyl-2-(4-hydrophenyl)hydrazine |
| H-3 | 1-acetyl-2-(4-aminophenyl)hydrazine |
| H-4 | 1-acetyl-2-(4-methylphenyl)hydrazine |
| H-5 | 1-acetyl-2-(4-acetamidophenyl)hydrazine |
| H-6 | 1-acetyl-2-(4-benzamidophenyl)hydrazine |
| H-7 | 1-acetyl-2-(4-methoxyphenyl)hydrazine |
| H-8 | 1-acetyl-2-[4-(3-sulfobenzamido)phenyl]-hydrazine |
| H-9 | 1-acetyl-2-(4-phenylsulfamidophenyl)-hydrazine |
| H-10 | 1-acetyl-2-(4-methylsulfonamidophenyl)-hydrazine |
| H-11 | 1-phenylsulfonyl-2-phenylhydrazine |
| H-12 | 1-methylsulfonyl-2-phenylhydrazine |
| H-13 | 1-benzoyl-2-phenylhydrazine |
| H-14 | 1-benzoyl-2-(4-benzamidophenyl)hydrazine |
| H-15 | 1-ethoxalyl-2-phenylhydrazine |
| H-16 | 1-methylsulfonyl-2-(3-phenylsulfonamidophenyl)hydrazine |
| H-17 | 1-(4-acetamidophenylsulfonyl)-2-(1-naphthyl)hydrazine |
| H-18 | 1-ethylsulfonyl-2-(4-diethylaminophenyl)-hydrazine |
| H-19 | 1-phenylsulfonyl-2-(4-benzamido-2,5-diethoxyphenyl)hydrazine |
| H-20 | 5-(1-carbo-2-phenylhydrazino)-1-phenyl-3-pyrazolidone |
| H-21 | 2-(1-carbo-2-phenylhydrazino)furan |
| H-22 | 4-(1-carbo-2-phenylhydrazino)pyridine |
| H-23 | 2-(1-carbo-2-phenylhydrazino)benzothiazole |
| H-24 | 1-[2-(2,4-di-tert-amylphenoxy)-5-(3,5-disulfobenzamido)benzoyl]-2-phenylhydrazine |
| H-25 | 1-acetyl-2-{4-[5-amino-2-(2,4-di-tert-pentyl-phenoxy)benzamido]phenyl}hydrazine |
| H-26 | 1-lauroyl-2-phenylhydrazine |
| H-27 | 1-lauroyl-2-[4-(3-sulfobenzamido)-phenyl]hydrazine |
| H-28 | 1-methylsulfonyl-2-(4-octadecylphenyl)-hydrazine |
| H-29 | 1-octadecyloxalyl-2-phenylhydrazine |
| H-30 | 1-octadecyloxalyl-2-[4-(3-sulfobenzamido)phenyl]hydrazine |
| H-31 | 1-lauroyl-2-[4-(β-methylsulfonamidoethyl)phenyl]hydrazine |
| H-32 | 1-[3-(2,4-di-tert-amyl-x-sulfophenoxy)-benzoyl]-2-phenylhydrazine |
| H-33 | 5-{1-carbo-2-[4-(α-sulfostearamido)-phenyl]hydrazino}-1-phenyl-3-pyrazolidone |
| H-34 | Formaldehyde phenylhydrazone |
| H-35 | Formaldehyde 4-(β-methylsulfonamidoethyl)phenylhydrazone |
| H-36 | Mucochloric acid 4-(β-methylsulfonamidoethyl)phenylhydrazone |
| H-37 | Acetone 4-methylphenylhydrazone |
| H-38 | Benzaldehyde 4-(β-methylsulfonamidoethyl)phenylhydrazone |
| H-39 | Benzaldehyde 4-methoxyphenylhydrazone |
| H-40 | Benzaldehyde 4-(3-sulfobenzamido)phenylhydrazone |
| H-41 | Formaldehyde 4-methylsulfonamidophenylhydrazone |
| H-42 | Acetaldehyde 4-phenylsulfonamidophenylhydrazone |
| H-43 | p-tolualdehyde 4-diethylaminophenylhydrazone |
| H-44 | cinchoninaldehyde 4-acetamidophenylhydrazone |
| H-45 | 2-furaldehyde 4-methylsulfonamido-1-naphthylhydrazone |
| H-46 | Nicotinaldehyde 4-(3-methylsulfamylbenzamido)2,5-diethoxyphenylhydrazone |
| H-47 | Hendecanal 4-(α-sulfostearamido)phenylhydrazone |
| H-48 | 3-octadecyloxybenzaldehyde phenylhydrazone |
| H-49 | 3-octadecyloxybenzaldehyde 4-(3-sulfobenzamido)phenylhydrazone |
| H-50 | benzaldehyde 4-[5-(3,5-disulfo)-2-(2,4-di-tert-pentyl-phenoxy)benzamido]phenylhydrazone dipotassium salt |
| H-51 | oxyguargum 4-(β-methylsulfonamidoethyl)-phenylhydrazone |
| H-52 | 1-phenylacetyl-2-phenylhydrazine |
| H-53 | 1-formyl-2-p-tolylhydrazine |

In another preferred form of this invention the acylhydrazinophenylthiourea nucleating agents are employed in combination with N-substituted cycloammonium quaternary salts of the type disclosed by Kurtz, Harbison, Heseltine and Lincoln, cited above. Generally these compounds can be represented by the formula:

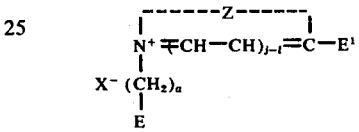

wherein:

1. Z represents the atoms necessary to complete a heterocyclic nucleus containing a heterocyclic ring of 5 to 6 atoms including the quaternary nitrogen atom, with the additional atoms of said heterocyclic ring being selected from carbon, nitrogen, oxygen, sulfur and selenium;
2. $j$ represents a positive integer of from 1 to 2;
3. $a$ represents a positive integer of from 2 to 6;
4. $X^-$ represents an acid anion;
5. E represents a member selected from:
   a. a formyl radical,
   b. a radical having the formula:

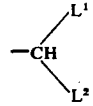

wherein each of $L^1$ and $L^2$, when taken alone, represents a member selected from an alkoxy radical and an alkylthio radical, and $L^1$ and $L^2$, when taken together, represent the atoms necessary to complete a cyclic radical selected from cyclic oxyacetals and cyclic thioacetals having from 5 to 6 atoms in the heterocyclic acetal ring, and
   c. a 1-hydrazonoalkyl radical; and
6. $E^1$ represents either a hydrogen atom, an alkyl radical, an aralkyl radical, an alkylthio radical or an aryl radical such as phenyl and naphthyl, and including substituted aryl radicals.

In certain preferred embodiments of this invention, the N-substituted, cycloammonium quaternary salts are those which contain N-substituted alkyl radicals having the terminal carbon atom substituted with a hydrazono radical, an acyl radical such as a formyl radical, an acetyl radical or a benzoyl radical, and those which have a dihydro—aromatic ring nucleus such as, for example, a dihydropyridinium nucleus.

Illustrative specific N-substituted quaternary ammonium salt nucleating agents useful in the practice of this invention include those set forth below in Table III.

TABLE III

| | |
|---|---|
| QAS- 1 | 3-(2-formylethyl)-2-methylbenzothiazolium salt |
| QAS- 2 | 3-(2-formylethyl)-2-methylnaphtho-[2,3-d]thiazolium salt |
| QAS- 3 | 3-(2-acetylethyl)-2-phenoxymethyl-benzothiazolium salt |
| QAS- 4 | 3-(2-acetylethyl)-2-benzylbenezoselenazolium salt |
| QAS- 5 | 1,2-dihydro-3-methyl-4-phenylpyrido-[2,1-b]benzothiazolium salt |
| QAS- 6 | 1,2-dihydro-3-methyl-4-phenylpyrido-[2,1-b]-5-phenylbenzoxazolium salt |
| QAS- 7 | 1,2-dihydro-3,4-dimethylpyrido[2,1-b]-benzothiazolium salt |
| QAS- 8 | 1,2-dihydro-3,4-diphenylpyrido[2,1-b]-benzoxazolium salt |
| QAS- 9 | 1,2-dihydro-2-butyl-3-methyl-4-phenyl-pyrido[2,1-b]-5-carbethoxybenzothiazolium salt |
| QAS-10 | 1,2-dihydro-3-methyl-4-phenylpyrido-[2,1-b]-5-(N-methyl-N-phenylcarbamido)-benzothiazolium salt |
| QAS-11 | 1,2-dihydro-3,4-dimethylpyrido[2,1-b]-5-(N-ethyl-N-octadecylcarbamido)benzothiazolium salt |
| QAS-12 | 3-(3,3-diethoxypropyl)-2-methylbenzothiazolium iodide |
| QAS-13 | 1-(2-formylethyl)lepidinium bromide |
| QAS-14 | 3-[3,3-di(ethylthio)propyl]-2-methyl-benzothiazolium iodide |
| QAS-15 | 3-(6,6-diethoxy-n-hexyl)-2-methylnaphtho-[2,1-d]thiazolium bromide |
| QAS-16 | 3-[2-(1,3-dioxan-2-yl)ethyl]-2-methyl-benzoselenazolium bromide |
| QAS-17 | 3-[3-1,3-dioxolan-2yl)propyl]-2-phenyl-benzimidazolium perchlorate |
| QAS-18 | 5-chloro-3-(2-formylethyl)-2-methylbenzothiazolium bromide |
| QAS-19 | 3-[3,3-di(ethylthio)propyl]-2-methyl-benzothiazolium iodide |
| QAS-20 | 3-(6,6-diethoxy-n-hexyl)-2-methyl-naphtho[2,1-d]thiazolium bromide |
| QAS-21 | 3-[2(1,3-dithiolan-2-yl)ethyl]-2-methyl-benzothiazolium iodide |
| QAS-22 | 3-(3,3-diethoxypropyl)-2-ethylthio-naphtho[2,3-d]thiazolium methylsulfate |
| QAS-23 | 3-[3-(1,3-dioxolan-2-yl)propyl]-1-ethyl-2-phenyl-benzimidazolium perchlorate |

To form a photographic element according to the present invention it is merely necessary to coat onto a conventional photographic support a radiation-sensitive composition comprised of internal latent image silver halide grains and an acylhydrazinophenylthiourea nucleating agent. Conventional photographic supports, including film and paper photographic supports, are disclosed in Product Licensing Index, cited above, paragraph X.

A simple exposure and development process can be used to form a direct-positive image. In one embodiment, a photographic element comprising at least one layer of a silver halide composition as described above can be imagewise exposed and then developed in a silver halide surface developer.

It is understood that the term "surface developer" encompasses those developers which will reveal the surface latent image on a silver halide grain, but will not reveal substantial internal latent image in an internal image-forming emulsion, and under the conditions generally used develop a surface-sensitive silver halide emulsion. The surface developers can generally utilize any of the silver halide developing agents or reducing agents, but the developing bath or composition is generally substantially free of a silver halide solvent (such as water-soluble thiocyanates, water-soluble thioethers, thiosulfates, ammonia and the like) which will crack or dissolve the grain to reveal substantial internal image. Low amounts of excess halide are sometimes desirable in the developer or incorporated in the emulsion as halide-releasing compounds, but high amounts of iodide or iodide-releasing compounds are generally avoided to prevent substantial cracking of the grain.

Typical silver halide developing agents which can be used in the developing compositions of this invention include hydroquinones, catechols, aminophenols, 3-pyrazolidones, ascorbic acid and its derivatives, reductones, phenylenediamines and the like or combinations thereof. The developing agents can be incorporated in the photographic elements wherein they are brought in contact with the silver halide after imagewise exposure; however, in certain embodiments they are preferably employed in the developing bath.

The developing compositions used in the process of this invention can also contain certain antifoggants and development restrainers, or optionally they can be incorporated in layers of the photographic element. For example, in some applications improved results can be obtained when the direct-positive emulsions are processed in the presence of certain antifoggants as disclosed in U.S. Pat. No. 2,497,917, which is incorporated herein by reference.

Typical useful antifoggants include benzotriazoles, such as benzotriazole, 5-methylbenzotriazole, 5-ethyl-benzotriazole and the like, benzimidazoles such as 5-nitrobenzimidazole, and the like, benzothiazoles such as 5-nitrobenzothiazole, 5-methylbenzothiazole and the like, heterocyclic thiones such as 1-methyl-2-tetrazoline-5-thione and the like, triazines such as 2,4-dimethylamino-6-chloro-5-triazine and the like, benzoxazoles such as ethylbenzoxazole and the like, and pyrroles such as 2,5-dimethylpyrrole and the like.

In certain embodiments, good results are obtained when the elements are processed in the presence of high levels of the antifoggants mentioned above. When antifoggants such as benzotriazoles are used, good results can be obtained when the processing solution contains up to 5 g/l and perferably 1 to 3 g/l; when they are incorporated in the photographic element, concentrations of up to 1,000 mg/mole of Ag and preferably concentrations of 100 to 500 mg/mole of Ag are employed.

It is, of course, known in the art that nucleating agents can be incorporated into surface developers in forming direct-positive images. While the acylhydrazinophenylthiourea nucleating agents could conceivably be incorporated into surface developers, it is our view that superior results are obtainable by incorporating the acylhydrazinophenylthiourea nucleating agents in the photographic element prior to development. It is, however, recognized that the other conventional nucleating agents discussed above for use in combination with the acylhydrazinophenylthiourea nucleating agents could be incorporated in the surface developer, wholly or partially, rather than being incorporated in the photographic element. It is preferred that the nucleating agents be entirely incorporated in the photographic element as opposed to the surface developer in most applications.

This invention may be used with elements designed for color photography for example, elements containing color-forming couplers such as those described in U.S. Pat. Nos. 2,376,679 by Frohlich et al.; 2,322,027 by Jelley et al.; 2,801,171 by Fierke et al.; 2,698,794 by Godowsky; 3,227,554 by Barr et al. and 3,046,129 by Graham et al.; or elements to be developed in solutions containing color-forming couplers such as those described in U.S. Pat. Nos. 2,252,718 by Mannes et al., 2,592,243 by Carroll et al. and 2,950,970 by Schwan et al.; and in false-sensitized color materials such as those described in U.S. Pat. No. 2,763,549 by Hanson.

This invention is useful with photographic elements used in image transfer processes or in image transfer film units. Generally the invention can be used with the color image transfer processes and the film units as described in Whitmore U.S. Pat. Nos. 3,227,550 and 3,227,552 issued Jan. 4, 1966; U.S. Pat. No. 2,983,606; U.S. Pat. No. 2,543,181; Whitmore Canadian Pat. No. 674,082; Belgian Pat. Nos. 757,959 and 757,960 both issued Apr. 23, 1971, and the like.

The silver halide emulsions as described herein are particularly useful in combination with negative working image dye providing materials; i.e., those materials which produce a negative pattern of transferred image dye when used in combination with a negative-working silver halide emulsion. Typical useful negative-working image dye providing materials are disclosed in Fleckenstein U.S. Published Application No. B 351,673, Jan. 28, 1975;; U.S. Pat. No. 3,698,897, issued Oct. 17, 1972, of Gompf and Lum; U.S. Pat. No. 3,728,113, issued Apr. 17, 1973, of Becker et al.; U.S. Pat. No. 3,725,062, issued Apr. 3, 1973, of Anderson and Lum; U.S. Pat. No. 3,148,062, issued Sept. 8, 1964, of Whitmore et al.; U.S. Pat. Nos. 3,628,952 and 3,844,785; and German OLS No. 2,317,134.

The direct positive silver halide emulsions of this invention are preferably used in combination with negative-working dye providing materials because the combination produces a positive transfer image. However, it is recognized that the direct positive emulsions can also be used with positive-working image dye providing materials such as dye developers as disclosed in U.S. Pat. No. 2,983,606, oxichromic developers as disclosed in U.S. Pat. No. 3,880,658, shifted dye developers as disclosed in Hinshaw U.S. Ser. No. 534,966, filed Dec. 20, 1975, and the like. Positive images are obtained in the exposed silver halide emulsion layers while a transferred negative image is obtained where the direct positive emulsions are used in combination with negative-working image dye providing materials. Also, where the exposure is made of a negative image or through a negative image record, positive transfer images are obtained with the combination of direct positive emulsions and positive-working image dye providing materials.

Generally, the image-transfer film units in accordance with this invention comprise:

1. a photosensitive element comprising a support having thereon at least one layer containing a radiation-sensitive internal latent image silver halide and acylhydrazinophenylthiourea nucleating agent containing a layer as described above, preferably having associated therewith an image dye-providing material;

2. an image-receiving layer which can be located on a separate support and superposed or adapted to be superposed on said photosensitive element, or preferably can be coated as a layer in the photosensitive element, and means containing an alkaline processing composition adapted to discharge its contents within said film unit and wherein said film unit contains a silver halide developing agent so that the processing composition and developing agent when brought together form a silver halide surface developer.

In highly preferred embodiments, the film units of this invention contain a support having thereon a layer containing a blue-sensitive emulsion having associated therewith a yellow image dye-providing material, a red-sensitive silver halide emulsion having associated therewith a cyan image dye-providing material, and a green-sensitive emulsion having associated therewith a magenta image dye-providing material, and preferably all of said image dye-providing materials are initially immobile image dye-providing materials.

The terms "diffusible" (or "mobile") and "immobile" (or "nondiffusible") as used herein refer to compounds which are incorporated in the photographic element and, upon contact with an alkaline processing solution, are substantially diffusible or substantially immobile, respectively, in the hydrophilic colloid layers of a photographic element.

The term "image dye-providing material" as used herein is understood to refer to those compounds which are employed to form dye images in photographic elements. These compounds include dye developers, shifted dyes, color couplers, oxichromic compounds, dye redox releasers, etc.

In one preferred embodiment, the silver halide emulsions of the invention are used in association with immobile redox dye-releaser image dye-providing compounds. The immobile redox dye-releasers undergo oxidation followed, in certain instances, by hydrolysis to provide an imagewise distribution of a mobile image dye. Compounds of this type can be used with direct-positive emulsions to form negative image records in the exposed photographic element and will provide a positive image in diffusible dye for transfer to an image-receiving layer, such as in an image-transfer film unit. Typical useful compounds of this type are disclosed in Whitmore et al. Canadian Pat. No. 602,607, issued Aug. 2, 1960; Fleckenstein et al. U.S. published application No. B 351,700, Jan. 28, 1975; and U.S. Pat. Nos. 3,698,897, 3,728,113, 3,725,062, 3,227,552, 3,443,939, 3,443,940 and 3,443,941, and the like, all of which are incorporated herein by reference. Where the receiver layer is coated on the same support with the photosensitive silver halide layers, the support is preferably a transparent support, an opaque layer is preferably positioned between the image-receiving layer and the photosensitive silver halide layer, and the alkaline processing composition preferably contains an opacifying substance such as carbon or a pH-indicator dye which is discharged into the film unit between a dimensionally stable support or cover sheet and the photosensitive element.

In certain embodiments, the cover sheet can be superposed or is adapted to be superposed on the photosensitive element. The image-receiving layer can be located on the cover sheet so that it becomes an image-receiving element. In certain preferred embodiments where the image-receiving layer is located in the photosensitive element, a neutralizing layer is located on the cover sheet.

A means for containing the alkaline processing solution can be any means known in the art for this purpose, including rupturable containers positioned at the point of desired discharge of its contents into the film unit and adapted to be passed between a pair of juxtaposed rollers to effect discharge of the contents into the film unit, frangible containers positioned over or within the photosensitive element, hypodermic syringes, and the like.

It is known in the art that neutralizing layers containing acidic materials, such as polymeric acids, monomeric acids, hydrolyzable materials and the like, can be positioned within an image-transfer film unit to effect shutdown of development of silver halide and transfer of the image dye-providing substance. Neutralizing layers can also be used in the film units of the present invention, including acid layers positioned behind timing layers to delay neutralization of the element, acid layers positioned near the image-receiving layer, acid layers on a cover sheet used to distribute the processing composition uniformly over the photosensitive element, acid layers within the photosensitive element, and the like.

The photographic emulsions and elements of this invention are described by the generic designation direct-positive. The term "direct reversal" has recently been employed in the art to distinguish direct-positive emulsions and elements which contain unfogged silver halide grains and nucleating agents from direct-positive silver halide emulsions and elements containing surface fogged silver halide grains. It is to be understood that this invention is directed to direct-reversal photographic emulsions and elements.

The invention can be further illustrated by the following examples.

EXAMPLES

1. 1-Formyl-2-(4-nitrophenyl)hydrazine

4-Nitrophenylhydrazine (9.2 g, 0.06 mole), sodium formate (4.08 g, 0.06 mole), and ethyl formate (148 g, 2.00 moles) were mixed in ethanol (40 ml) and fumaric acid (30 ml). The mixture was heated on a steam bath; the volume of the mixture was reduced to approximately 100 ml by continued boiling. The hydrazide product crystallized out of the concentrated reaction mixture upon cooling. The product was filtered off, washed with ethanol, and dried. Yield 10.2 g (94%), m.p. 183°–185° C.

2. 1-Benzoyl-2-(4-nitrophenyl)hydrazine

4-Nitrophenylhydrazine (15.0 g, 0.10 mole) and benzoic anhydride (22.6 g, 0.10 mole) were mixed in benzene (100 ml) and the mixture was refluxed for 2 hours. The reaction mixture was chilled in ice and then filtered. The solid was washed with ethanol and allowed to dry. The material was recrystallized from ethanol. Yield 20.5 g (80%), m.p. 194°–195° C.

3. 1-Formyl-2-(4-aminophenyl)hydrazine

1-Formyl-2-(4-nitrophenyl)hydrazine (10.2 g, 0.056 mole) and 10% palladium/charcoal (catalytic amount) were suspended in ethanol (500 ml) in a Parr shaker bottle. The reaction mixture was hydrogenated at room temperature until hydrogen uptake ceased. The reaction mixture was filtered and the solvent was evaporated from the filtrate leaving a white crystalline powder. Yield 7.1 g (84%), m.p. 122°–125° C.

4. 1-Benzoyl-2-(4-aminophenyl)hydrazine

1-Benzoyl-2-(4-nitrophenyl)hydrazine (14.3 g, 0.056 mole) and 10% palladium/charcoal (catalytic amount) were suspended in ethanol (300 ml) in a Parr shaker bottle. The reaction mixture was hydrogenated at room temperature until hydrogen uptake ceased. The reaction mixture was filtered and the solvent was evaporated from the filtrate leaving a tan crystalline powder. Yield 11.5 g (90%), m.p. 134°–136° C.

5. 1-Acetyl-2-(4-benzalaminophenyl)hydrazine

1-Acetyl-2-(4-aminophenyl)hydrazine (8.25 g, 0.05 mole) and benzaldehyde (5.3 g, 0.05 mole) were mixed in ethanol (50 ml). The mixture was stirred thoroughly and was warmed to approximately 75° C for one-half hour. The addition product precipitated out of the reaction mixture. The mixture was chilled in ice and then filtered. The solid was washed with ether and dried. The product was a white cyrstalline powder. Yield 12.0 g (94%), m.p. 172°–174° C.

6. 1-Acetyl-2-(4-benzylaminophenyl)hydrazine

1-Acetyl-2-(4-benzalaminophenyl)hydrazine (5.1 g, 0.02 mole) and platinum oxide (catalytic amount) were suspended in ethanol (200 ml) in a Parr shaker bottle. The reaction mixture was hydrogenated at room temperature until hydrogen uptake ceased. The reaction mixture was filtered and the solvent was evaporated from the filtrate leaving a white crystalline powder. Yield 4.7 g (92%), m.p. 118°–120° C.

7. 1-Acetyl-2-[4-(4-methoxybenzyl)aminophenyl]hydrazine

Procedures (5) and (6) above were repeated, but with 4-methoxybenzaldehyde substituted for benzaldehyde.

8. 1,3-Bis[4-(2-formylhydrazino)phenyl]thiourea (NA-1)

$$\underset{HC}{\overset{O}{\|}}-NH-NH-\bigcirc-NH-\underset{C}{\overset{S}{\|}}-NH-\bigcirc-NH-NH-\underset{CH}{\overset{O}{\|}}$$

$C_{15}H_{16}N_6O_2S$

Sodium carbonate (2.1 g, 0.02 mole) was dissolved in water (100 ml). Bis(carboxymethyl)trithiocarbonate (4.5 g, 0.02 mole) was added portionwise with vigorous stirring. The pH of the reaction mixture was adjusted to 9.5 by the addition of sodium carbonate. The mixture was then heated to approximately 95° C. 1-Formyl-2-(4-aminophenyl)hydrazine (6.5 g, 0.043 mole) was added in one portion to the reaction mixture. Stirring was continued for five minutes. The reaction mixture was chilled, the solid was filtered off, washed thoroughly with water and dried. Yield 4.5 g (66%), m.p. 212°–214° C.

9. 1,3-Bis[4-(2-acetylhydrazino)phenyl]thiourea (NA-2)

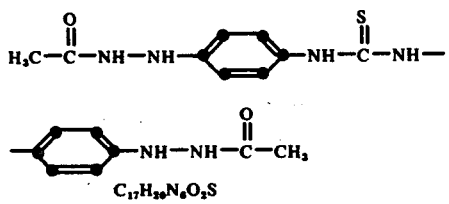

$C_{17}H_{20}N_6O_2S$

Sodium carbonate (100 g, 0.96 mole) was dissolved in water (1 liter). Bis(carboxymethyl)trithiocarbonate (55 g, 0.24 mole) was added portionwise with stirring. The solution was heated to 90° C and 1-acetyl-2-(4-aminophenyl)hydrazine (78 g, 0.47 mole) was added in one portion. After stirring at 90° C for 30 min., the product was filtered off, washed thoroughly with water and dried. Yield 50 g (56%), m.p. 234°–236° C.

10. 1,3-Bis[4-(2-benzoylhydrazino)phenyl]thiourea (NA-6)

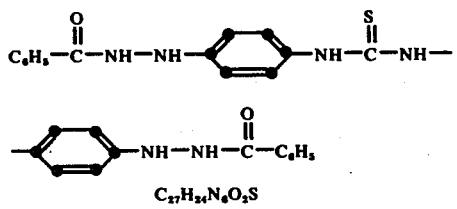

$C_{27}H_{24}N_6O_2S$

Sodium carbonate (4.65 g, 0.044 mole) was dissolved in a solvent mixture of water (95 ml) and ethanol (30 ml). Bis(carboxymethyl)trithiocarbonate (2.5 g, 0.011 mole) was added portionwise. Vigorous stirring of the reaction mixture was maintained until all solid was dissolved. It was then heated to 80°–85° C and 1-benzoyl-2-(4-aminophenyl)hydrazine (5.0 g, 0.022 mole) was added in one portion. Stirring and heating were maintained for 1½ hour and the reaction mixture was then chilled. The solid was removed by filtration, washed and dried. Yield 2.05 g (37%), m.p. 185°–187° C.

11. 1-[4-(2-Formylhydrazino)phenyl]-3-methylthiourea (NA-11)

$C_9H_{12}N_4OS$

1-Formyl-2-(4-aminophenyl)hydrazine (1.51 g, 0.01 mole) and methyl isothiocyanate (0.73 g, 0.01 mole) were mixed in ethanol (20 ml) and the mixture was refluxed for 30 minutes. The mixture was chilled in ice, and water was added to precipitate the product. The product came out of solution in an oily form, but solidified upon scratching and standing. The solid material was filtered off and washed thoroughly with ether. The product was dried to give a white crystalline powder. Yield 1.3 g (58%), m.p. 176°–178° C.

12. 3-Butyl-1-[4-(2-formylhydrazino)phenyl]thiourea (NA-12)

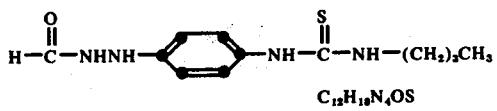

$C_{12}H_{18}N_4OS$

1-Formyl-2-(4-aminophenyl)hydrazine (7.5 g, 0.05 mole) and butyl isothiocyanate (5.7 g, 0.05 mole) were mixed in ethanol (120 ml) and the mixture was refluxed for 30 minutes. The resulting solution was chilled in ice and upon scratching the product crystallized out as a white solid. The mixture was filtered and the solid was washed with ether. The product was dried to give a pale tan crystalline powder. Yield 9.8 g (74%), m.p. 129°–131° C.

13. 1-[4-(2-Acetylhydrazino)phenyl]-3-ethylthiourea (NA-13)

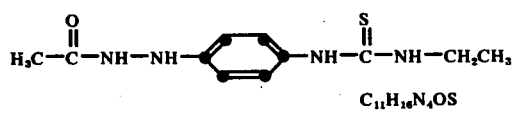

$C_{11}H_{16}N_4OS$

1-Acetyl-2-(4-aminophenyl)hydrazine (1.65 g, 0.01 mole) and ethyl isothiocyanate (0.87 g, 0.01 mole) were reacted according to procedure (11.). Yield 1.7 g (67%), m.p. 191°–193° C.

14. 3-Cyclohexyl-1-[4-(2-formylhydrazino)phenyl]thiourea (NA-14)

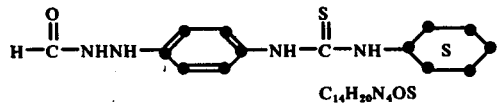

$C_{14}H_{20}N_4OS$

Procedure (12.) was employed with 1-formyl-2-(4-aminophenyl)hydrazine (7.5 g, 0.05 mole) and cyclohexyl isothiocyanate 7.1 g, 0.05 mole). Yield 9.6 g (66%), m.p. 158°–160° C.

15. 1-[4-(2-Formylhydrazino)phenyl]-3-phenylthiourea (NA-16)

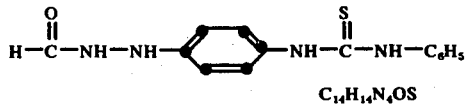

$C_{14}H_{14}N_4OS$

1-Formyl-2-(4-aminophenyl)hydrazine (30 g, 0.20 mole) was dissolved in acetonitrile (550 ml) with heat. Phenyl isothiocyanate (28 g, 0.22 mole) was added in one portion. The mixture was refluxed for 5 minutes and then chilled. The solid was filtered off, washed with acetonitrile and dried at 75° C. Yield 52 g (91%), m.p. 188°–188.5° C.

16. 1[4-(2-Acetylhydrazino)phenyl]-3-phenylthiourea (NA-17)

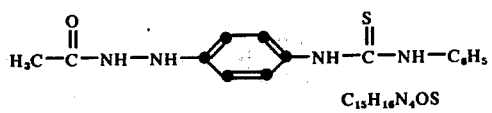

$C_{15}H_{16}N_4OS$

1-Acetyl-2-(4-aminophenyl)hydrazine (8.25 g, 0.05 mole) and phenyl isothiocyanate (6.8 g, 0.05 mole) were suspended in acetonitrile (100 ml). The resulting mixture was heated at reflux with stirring for 5 minutes. The product separated from solution as a white solid. After chilling, the product was removed from the reaction mixture by filtration and washed thoroughly with ether. Yield 14.5 g (96%), m.p. 205°–207° C.

17. 1-[4-(2-Benzoylhydrazino)phenyl]-3-phenylthiourea (NA-15)

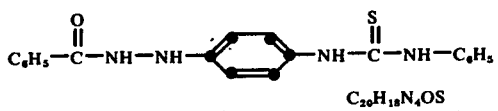

$C_{20}H_{18}N_4OS$

1-Benzoyl-2-(4-aminophenyl)hydrazine (1.14 g, 0.005 mole) and phenyl isothiocyanate (2.7 g, 0.02 mole) were mixed together and heated until contents became fluid. Gentle warming was continued for a few minutes and the reaction mixture was then chilled and diluted with ether. After some stirring and scratching, the product precipitated from solution. It was filtered off, washed thoroughly with ether and dried. Yield 1.7 g (94%), m.p. 149°–151° C.

18. 3-Benzyl-1-[4-(2-formylhydrazino)phenyl]thiourea (NA-19)

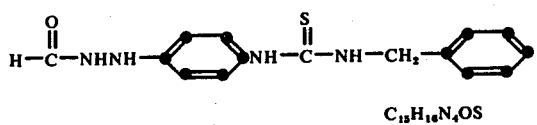

$C_{15}H_{16}N_4OS$

1-Formyl-2-(4-aminophenyl)hydrazine (1.51 g, 0.01 mole) and benzyl isothiocyanate (1.49 g, p.01 mole) were mixed in ethanol (30 ml) and the mixture was refluxed for 20 minutes. The product separated from solution as a white solid. The reaction mixture was chilled in ice and the solid was collected by filtration. The product was washed thoroughly with ether and then was dried. Yield 2.5 g (83%), m.p. 152°–154° C.

19. 1-[4-(2-Formylhydrazino)phenyl]-3-heptylthiourea (NA-20)

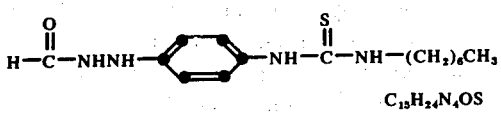

$C_{15}H_{24}N_4OS$

Procedure (12) was employed with 1-formyl-2-(4-aminophenyl)hydrazine (1.51 g, 0.01 mole) and heptyl isothiocyanate (1.57 g, 0.01 mole). The product was recrystallized from ethanol. Yield 1.5 g (49%), m.p. 148°–150° C.

20. 1-[4-(2-Formylhydrazino)phenyl]-3-decylthiourea (NA-21)

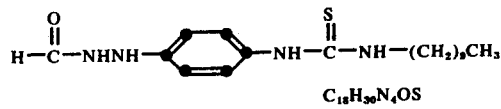

$C_{18}H_{30}N_4OS$

Procedure (12.) was employed with 1-formyl-2-(4-aminophenyl)hydrazine (1.51 g, 0.01 mole) and decyl isothiocyanate (1.99 g, 0.01 mole). Yield 2.4 g (69%), m.p. 150°–152° C.

21. 3-(4-cyanophenyl)-1-[4-(2-formylhydrazino)phenyl[-thiourea (NA-22)

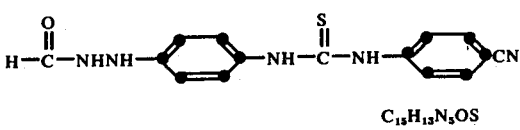

$C_{15}H_{13}N_5OS$

Procedure (18.) was employed with 1-formyl-2-(4-aminophenyl)hydrazine (1.5 g, 0.01 mole) and 4-cyanophenyl isothiocyanate (1.6 g, 0.01 mole). Yield 2.2 g (71%), m.p. 180°–182° C.

22. 1-[4-(2-Formylhydrazino)phenyl[-3-(4-methoxyphenyl)thiourea (NA-23)

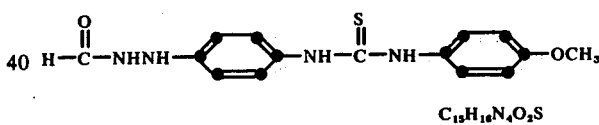

$C_{15}H_{16}N_4O_2S$

Procedure (18.) was employed with 1-formul-2-(4-aminophenyl)hydrazine (1.51 g, 0.01 mole) and 4-methoxyphenyl isothiocyanate (1.65 g, 0.01 mole). Yield 1.7 g (53%), m.p. 198°–200° C.

23. 1-Formyl-2-(4-nitro-2-methoxyphenyl)hydrazine

2-Methoxy-4-nitrophenylhydrazine (11.0 g, 0.06 mole; prepared by reduction of the diazonium salt from 2-methoxy-4-nitroaniline), sodium formate (4.1 g, 0.06 mole) and ethyl formate (148 g, 2.00 moles) were mixed in ethanol (40 ml) and formic acid (30 ml). The mixture was heated on a steam bath; the volume of the mixture was reduced to approximately 100 ml by continued boiling. The hydrazide produce crystallized out of the concentrated reaction mixture upon cooling. The product was filtered off, washed with ethanol, and dried. Yield 8.5 g (66%), m.p. 189°–191° C.

24. 1-Formyl-2-(4-amino-2-methoxyphenyl)hydrazine

Procedure (3.) was employed with 1-formyl-2-(4-nitro-2-methoxyphenyl)hydrazine (4.0 g, 0.019 mole). Yield 2.5 g (74%), m.p. 113°–116° C.

25.
1-[4-(2-Formylhydrazino)-3-methoxyphenyl]-3-phenylthiourea (NA-24)

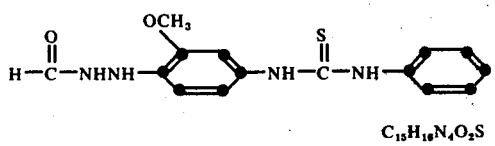

Procedure (18.) was employed with 1-formyl-2-(4-amino-2-methoxyphenyl)hydrazine (1.0 g; 0.0056 mole) and phenyl isothiocyanate (0.75 g, 0.0056 mole). Yield 0.90 g (51%), m.p. 183°–184° C.

26.
3-Butyl-1-[4-(2-formylhydrazino)-3-methoxyphenyl]-thiourea (NA-25)

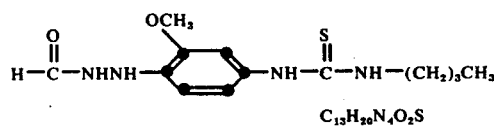

Procedure (12.) was employed with 1-formyl-2-(4-amino-2-methoxyphenyl)hydrazine (1.2 g, 0.0066 mole) and butyl isothiocyanate (0.76 g, 0.006 mole). Yield 0.90 g (46%), m.p. 130°–132° C.

27.
3-cyclohexyl-1-[4-(2-formylhydrazino)-3-methoxyphenyl]thiourea (NA-26)

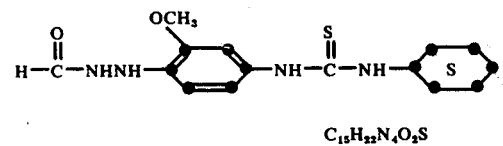

Procedure (11.) was employed with 1-formyl-2-(4-amino-2-methoxyphenyl)hydrazine (1.2 g, 0.0066 mole) and cyclohexyl isothiocyanate (0.93 g, 0.0066 mole). Yield 0.50 g (24%), m.p. 131°–133° C.

28.
1-[4-(2-Formylhydrazino)-3-methoxyphenyl]-3-(4-methoxyphenyl)thiourea (NA-27)

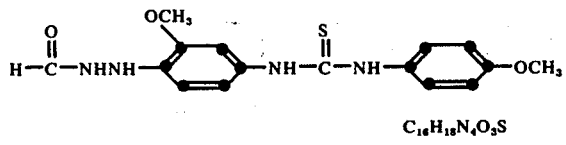

Procedure (18.) was employed with 1-formyl-2-(4-amino-2-methoxyphenyl)hydrazine (1.2g, 0.006 mole) and 4-methoxyphenyl isothiocyanate (1.1 g, 0.0066 mole). Yield 1.6 g (70%), m.p. 160°–162° C.

29. 2-(4-Nitrophenyl)-1-trifluoroacetylhydrazine

4-Nitrophenylhydrazine (7.6 g, 0.05 mole) was mixed with benzene (150 ml) and the resulting mixture was stirred under nitrogen at room temperature. A solution of trifluoroacetic anhydride (10.5 g, 0.05 mole) in benzene (50 ml) was added dropwise. The mixture was stirred vigorously as a thick yellow solid precipitated out. After the addition was complete, the mixture was stirred for one more hour at room temperature. The mixture was filtered and the solid was washed with benzene and then allowed to dry. Yield 12.2 g (97%), m.p. 115°–117° C.

30. 2-(4-Aminophenyl)-1-trifluoroacetylhydrazine 2-(4-Nitrophenyl)-1-trifluoroacetylhydrazine (2.5 g, 0.01 mole) and platinum oxide (84%, catalytic amount) were mixed in ethanol (100 ml) and ethyl acetate (100 ml) in a Parr shaker bottle. The reaction mixture was hydrogenated at room temperature until hydrogen uptake ceased. The reaction mixture was filtered and the solvent was evaporated from the filtrate leaving a brown semisolid. Yield 2.0 g (91%), no m.p. was taken on this material. Spectral data verified its structure.

31.
3-Phenyl-1-[4-(2-trifluoroacetylhydrazino)phenyl]thiourea (NA-28)

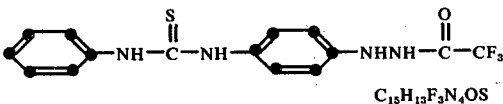

2-(4-Aminophenyl)-1-trifluoroacetylhydrazine (2.0 g, 0.0091 mole) and phenyl isothiocyanate (1.2 g, 0.0091 mole) were mixed together in ethanol (25 ml) and the mixture was heated to reflux for 20 minutes. A white solid precipitated out of the mixture during the heating. The mixture was chilled in ice and the solid was filtered off, washed with ethanol, and dried. Spectral data on this material indicated that it was not the desired product. The filtrate from above was diluted with water and a second solid material formed. This material was filtered off, washed with water and dried to give a white crystalline powder. Yield 0.80 g (25%), m.p. 172°–174° C. Spectral evidence verified that this substance was the desired product.

32. 1-(4-Chlorobenzoyl)-2-(4-nitrophenyl)hydrazine

4-Nitrophenylhydrazine (32.0 g, 0.21 mole) was slurried in acetonitrile (500 ml) and the mixture was cooled to 0° C. A solution of 4-chlorobenzoyl chloride (17.5 g, 0.10 mole) in acetonitrile (25 ml) was added dropwise to the cooled slurry. The reaction mixture was allowed to stand overnight. The mixture was filtered and the solid was washed with acetonitrile, then thoroughly with water. The product was recrystallized from acetonitrile and decolorized with charcoal to give a pale yellow solid. Yield 24.8 g (85%), m.p. 245.5°–248.5° C.

33. 1-(4-Chlorobenzoyl)-2-(4-aminophenyl)hydrazine hydrochloride 1-(4-Chlorobenzoyl)-2-(4-nitrophenyl)hydrazine (2.92g, 0.01 mole) and 5% palladium or barium sulfate (catalytic amount) were suspended in a mixture of ethanol (350 ml) and concentrated hydrochloric acid (5 ml) in a Parr shaker bottle. The reaction mixture was hydrogenated at room temperature until the theoretical amount of hydrogen had been taken up. The reaction mixture was filtered and the solvent was evaporated from the filtrate leaving a tan solid. Yield 2.9 g (99%), m.p. 209° C (dec.).

34.
1- 4-[2-(4-Chlorobenzoyl)hydrazino]phenyl -3-phenylthiourea (NA-30)

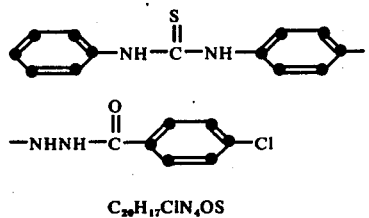

1-(4-Chlorobenzoyl)-2-(4-aminophenyl)hydrazine hydrochloride (2.0 g, 0.0067 mole) was mixed with ethanol (125 ml) and water (25ml). Phenyl isothiocyanate (1.1 g, 0.01 mole) was added to the mixture along with sodium acetate (0.82 g, 0.1 mole) in water (10 ml). The reaction mixture was stirred and refluxed for 5 minutes, then was stirred at room temperature for 1½ hours. The mixture was chilled in ice and then filtered. The product was washed with ethanol and dried to give an off-white solid. Yield 1.9 g (71%), m.p. 197.5°–199° C.

35.
1- 4-[2-(4-Cyanobenzoyl)hydrazino]phenyl -3-phenylthiourea (NA-29)

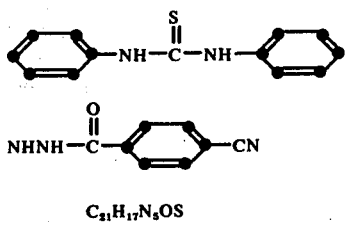

Procedures (32.), (33.) and (34.) were repeated, but with 4-cyanobenzoyl chloride substituted for 4-chlorobenzoyl chloride. Yield 2.0 g (65%), m.p. 184°–185° C.

36.
1-X--[4-Fluorobenzoyl)hydrazino]phenyl -3-phenylthiourea (NA-31)

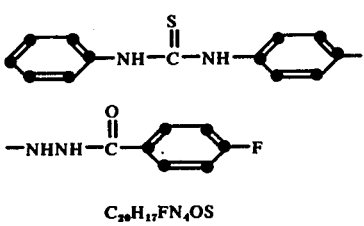

Procedures (32.), (33.) and (34.) were repeated, but with 4-fluorobenzoyl chloride substituted for 4-chlorobenzoyl chloride. Yield 2.3 g (66%), m.p. 193°–194° C.

37.
1- 4-[2-(4-Methylbenzoyl)hydrazino]phenyl -3-phenylthiourea (NA-32)

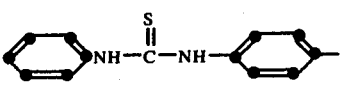

-continued

Procedures (32.), (33.) and (34.) were repeated, but with 4-methylbenzoyl chloride substituted for 4-chlorobenzoyl chloride. Yield 1.9 g (50%), m.p. 185.5°–187° C.

38.
1- 4-[2-(4-Methoxybenzoyl)hydrazino]phenyl -3-phenylthiourea (NA-33)

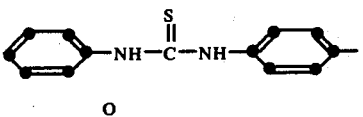

Procedures (32.), (33.) and (34.) were repeated, but with 4-methoxybenzoyl chloride substituted for 4-chlorobenzoyl chloride. Yield 2.5 g (71%), m.p. 177.5°–178.5° C.

39.
3-Benzyl-1- 4-[2-(4-chlorobenzoyl)hydrazino]phenylthiourea (NA-34)

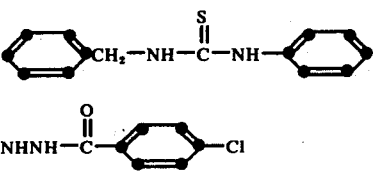

1-(4-Chlorobenzoyl)-2-(4-aminophenyl)hydrazine hydrochloride (1.5 g, 0.005 mole) was dissolved in hot ethanol (30 ml) under a nitrogen atmosphere. Benzyl isothiocyanate (0.82 g, 0.0055 mole) and potassium acetate (0.6 g, 0.006 mole) were added and the mixture was refluxed under nitrogen for 2 hours. The reaction mixture was cooled to room temperature, diluted with water (10–15 ml.) and chilled in ice. The product was filtered off, washed with ethanol and dried. Recrystallization of the product from acetonitrile gave an off-white solid. Yield 1.25 g (62%), m.p. 197°–199° C.

40.
3-Benzyl-1- 4-[2-(4-fluorobenzoyl)hydrazino]phenylthiourea (NA-35)

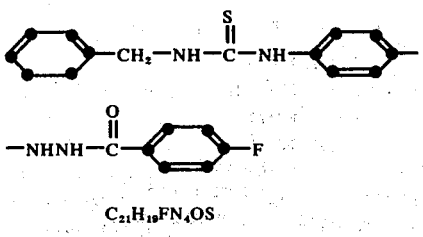

Procedure (39.) above was repeated, but with 1-(4-fluorobenzoyl)-2-(4-fluorobenzoyl-2-(4-aminophenyl)hydrazine hydrochloride substituted for 1-(4-chlorobenzoyl)-2-(4-aminophenyl)hydrazine hydrochloride. Yield 0.7 g (35%), m.p. 185.5°–187.5° C.

41.

1-[3-(3-(2-Formylhydrazino)phenyl]-3-phenylthiourea (NA-36)

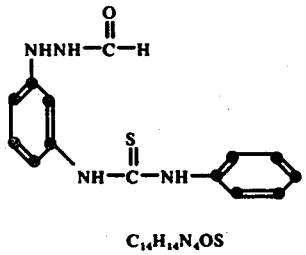

Procedures (1.), (3.), and (11.) were employed, but with 3-nitrophenylhydrazine in place of 4-nitrophenylhydrazine and phenyl isothiocyanate in place of methyl isothiocyanate. Yield 2.8 g (62%), m.p. 143°–145° C.

42.

1-[3-(2-Formylhydrazino)phenyl]-3-(4-methoxyphenylthiourea (NA-37)

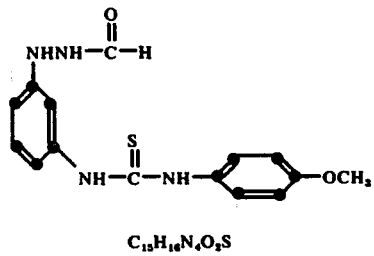

Procedures (1.), (3.) and (11.) were employed, but with 3-nitrophenylhydrazine in place of 4-nitrophenylhydrazine and with 4-methoxyphenyl isothiocyanate in place of methyl isothiocyanate. Yield 2.7 g (64%), m.p. 150°–152° C.

43.

1-[2-(2-Formylhydrazino)phenyl]-3-phenylthiourea (NA-38)

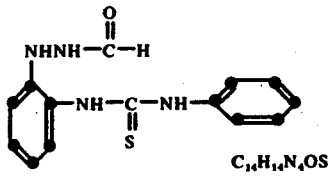

Procedures (1.), (3.) and (18.) were employed, but with 2-nitrophenylhydrazine in place of 4-nitrophenylhydrazine and with phenyl isothiocyanate in place of benzyl isothiocyanate. Yield 1.8 g (63%), m.p. 224°–226° C.

44.

1-[4-(2-Acetylhydrazino)phenyl]-1-benzyl-3-phenylthiourea (NA-40)

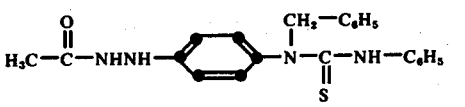

1-Acetyl-2-(4-benzylaminophenyl)hydrazine (2.80 g, 0.011 mole) and phenylisothiocyanate (1.35 g, 0.01mole) were mixed in ethanol (25 ml) and the resulting mixture was refluxed for 5 minutes. The mixture was chilled in ice and water was added to precipitate the product. The product oiled out of solution, but became crystalline upon standing and scratching. The solid was filtered off and washed with water, then ether. After drying the product was a pale yellow crystalline powder. Yield 3.0 g (77%), m.p. 114°–117° C.

45.

1-[4-(2-Acetylhydrazino)phenyl]-1-(4-methoxybenzyl)-3-phenylthiourea (NA-42)

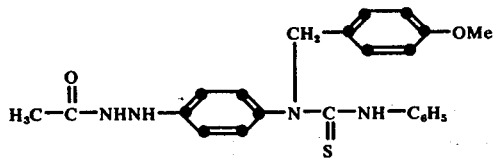

1-Acetyl-2-[4-(4-methoxybenzyl)aminophenyl]hydrazine (3.1 g, 0.011 mole) and phenylisothiocyanate (1.35 g, 0.01 mole) were mixed in ethanol (25 ml) and the resulting mixture was refluxed for 10 minutes. The mixture was chilled in ice and diluted with water. The product oiled out of solution, but upon standing and scratching the substance solidified. The solid material was filtered off, washed with water and allowed to dry. The material was stirred twice in a large volume of ether, then was filtered and washed with fresh ether. The product was a white powder. Yield 2.75 g (66%), m.p. 126°–128° C.

46. Comparison of single color photographic elements

A control integral, single color photographic element, Element 1, was prepared by coating the following layers in the order given on a poly(ethylene terephthalate) film support (coverages in parenthesis in g/m² unless indicated):

1. image-receiving layer of poly[styrene-co-N-benzyl-N,N-dimethyl-N-(3-maleimidopropyl)ammonium chloride] (2.2) and gelatin (2.2).
2. reflecting layer of titanium dioxide (21.5) and gelatin (2.2).
3. opaque layer of carbon black (2.7) and gelatin (1.7).
4. Compound A¹ (0.54) dispersed in gelatin (0.73).
5. blue-sensitive, direct-positive, internal image gelatin-silver bromide emulsion of the type described in U.S. Pat. No. 3,761,276; (1.1 Ag, 2.2 gelatin), 5-sec-octadecylhydroquinone-2-sulfonic acid (20 g/mole silver) and nucleating agent compound H-25 (2000 mg/mole silver).

Compound A

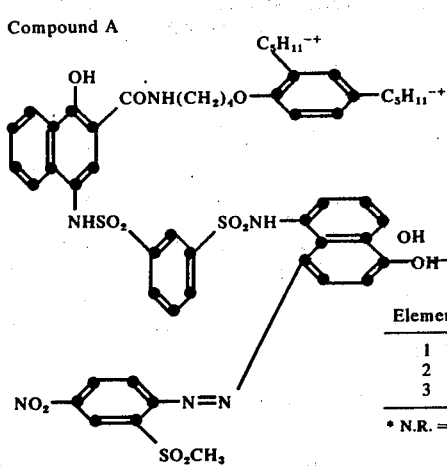

Element 2 was identical to Element 1 except that the 2000 mg/mole of nucleating agent H-25 was replaced with 4 mg/mole of the compound NA-1.

Element 3 was identical to Element 1 except that nucleating agent H-25 was replaced by 10 mg/mole of the compound NA-2.

The above-prepared photosensitive elements were then exposed to a tungsten light source through a graduated step tablet in a sensitometer. The following processing composition was employed in a pod and was spread between the photosensitive element and a transparent cover sheet described below at about 15° and 38° C by passing the transfer "sandwich" between a pair of juxtaposed rollers so that the liquid layer was about 0.1 mm in thickness.

The cover sheet was prepared by coating in the order recited the following layers on a poly(ethylene terephthalate) support:

1. a polyacrylic acid layer (15.5 g/m²)
2. a timing layer of a 95/5 mixture of cellulose acetate (40% acetyl) and poly(styrene-co-maleic anhydride (4.3 g/m²).

The processing composition was as follows:

| | |
|---|---|
| Potassium hydroxide | 56.0 g |
| 4-Hydroxymethyl-4-methyl-1-phenyl-3-pyrazolidone | 8.0 g |
| 5-Methylbenzotriazole | 2.4 g |
| t-Butylhydroquinone | 0.2 g |
| Sodium sulfite (anhyd) | 2.0 g |
| Carbon | 40.0 g |
| Hydroxyethylcellulose | 25.0 g |
| Water to make 1 liter | |

The results of the reflection densitometry read from the cyan image on the receiving layer through the film support of the laminated sandwich is shown in Table IV.

The nucleating agents NA-1 and -2 give excellent reversal image discrimination at extraordinarily low levels compared to the nonadsorbed prior art fogging agent H-25. Much more satisfactory Dmin values are obtained with NA-1 and NA-2 at 38° C with some loss in effective speed. The action of NA-2 was surprisingly insensitive to the difference in processing temperature in Dmax, Dmin and in relative speed.

TABLE IV

| Element | Nucleating Agent (Conc. mg/mole Ag) | | 150° C Process | | | 38° C Process | | |
|---|---|---|---|---|---|---|---|---|
| | | | $D_{max}$ | $D_{min}$ | Rel. Speed | $D_{max}$ | $D_{min}$ | Rel. Speed |
| 1 | H-25 Control | (2000) | 2.48 | 0.16 | 100 | 2.76 | fog | N.R.* |
| 2 | NA-1 | (4) | 1.82 | 0.16 | 79 | 2.48 | 0.22 | 26 |
| 3 | NA-2 | (10) | 1.98 | 0.16 | 45 | 2.18 | 0.28 | 37 |

* N.R. = Not Recorded

47. Additional Nucleating in Single Color Photographic Elements

A plurality of integral, single-color photographic elements were prepared in each instance by coating the following layers in the order given on a poly(ethylene terephthalate) film support (coverages in g/m² unless indicated):

1. image-receiving layer of poly(styrene-co-N-benzyl-N,N-dimethyl-N-vinylbenzylammonium sulfate-co-divinyl benzene) (2.3) and gelatin (2.3)
2. reflecting layer of titanium dioxide (16:1) and gelatin (2.6)
3. layer of gelatin (1.2)
4. gelatin (1.2) and dye-releasing redox compound having the formula:

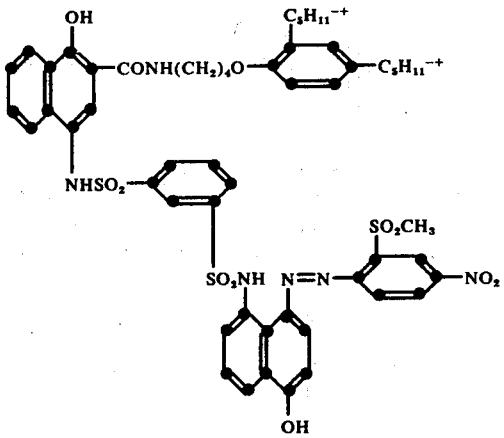

5. blue-sensitive, direct-positive, internal image gelatin-silver bromide emulsions of the type described in U.S. Pat. No. 3,761,276 (1.4 silver, 1.4 gelatin), 5-sec-octadecylhydroquinone-2-sulfonic acid (16 g/mole silver) and nucleating agent as given in Table V below.

Each of the above-described photographic elements was exposed to a tungsten light source through a graduated step tablet in a sensitometer. A processing composition contained in a pod was spread at about 23° C between the emulsion layer and a transparent cover sheet by passing the pod, the photographic element and the superimposed cover sheet between a pair of juxtaposed rollers so that the processing composition was forced from the pod and distributed between the cover sheet and the photographic element to form a liquid layer about 0.1 mm in thickness.

The cover sheet was prepared by coating the following layers in the order indicated onto a poly(ethylene terephthalate) film support:

1. an acid layer comprised of poly(n-butyl acrylate-coacrylic acid) (15.5) (70 weight percent acrylic acid);
2. a timing layer comprising 5-(2-cyanoethylthio)-1-phenyltetrazole (0.11), cellulose acetate (4.31) (40 weight percent acetyl) and poly(styrene-co-maleic anhydride) (0.11) and
3. polyacrylonitrile-co-vinylidene chloride-co-acrylic acid) (2.15).

The cover sheet was oriented so that the coated side was nearest the emulsion layer.

The pod contained the following processing composition:

| | |
|---|---|
| Potassium hydroxide | 47.0 g |
| Sodium hydroxide | 3.4 g |
| Methylhydroquinone | 0.1 g |
| t-butylhydroquinone | 0.3 g |
| 4-hydroxymethyl-4-methyl-1-phenyl pyrazolidone | 12.0 g |
| 5-methyl-1,2,3-benzotriazole | 3.8 g |
| carboxymethylcellulose | 66.8 g |
| dispersant | 8.8 g |
| sodium sulfite (anhydrous) | 1.0 g |
| benzyl alcohol | 1.0 g |
| carbon | 171.0 g |
| distilled water to total volume 1 liter. | |

The results of the reflection densitometry read from the yellow dye image on the receiving layer through film support are given in Table V.

Table V

| Nucleating Agent | Conc. (mg/mole silver) | $D_{max}$ | $D_{min}$ | Rel. Speed |
|---|---|---|---|---|
| NA-16 | 6.0 | 1.78 | 0.28 | 100 |
| NA-12 | 4.3 | 1.86 | 0.26 | 71 |
| NA-14 | 4.7 | 1.87 | 0.26 | 63 |
| NA-19 | 4.9 | 1.82 | 0.27 | 89 |
| NA-23 | 6.6 | 1.83 | 0.28 | 55 |
| NA-25 | 4.8 | 1.89 | 0.26 | 43 |
| NA-26 | 5.2 | 1.86 | 0.27 | 71 |
| NA-27 | 7.3 | 1.87 | 0.28 | 34 |
| NA-15 | 12.8 | 1.72 | 0.28 | 120 |
| NA-29 | 6.4 | 1.74 | 0.28 | 105 |
| NA-30 | 8.8 | 1.76 | 0.28 | 102 |
| NA-31 | 8.3 | 1.80 | 0.27 | 102 |
| NA-32 | 14.9 | 1.46 | 0.28 | 240 |
| NA-33 | 22.4 | 0.42 | 0.28 | N.R.* |
| NA-16 | 5.0 | 1.87 | 0.30 | 100 |
| NA-20 | 5.4 | 1.89 | 0.26 | 35 |
| NA-21 | 6.1 | 1.89 | 0.26 | 32 |
| NA-22[2] | 6.0 | 0.62 | 0.31 | N.R. |
| NA-16 | 5.0 | 1.79 | 0.48 | 100 |

Table V-continued

| Nucleating Agent | Conc. (mg/mole silver) | $D_{max}$ | $D_{min}$ | Rel. Speed |
|---|---|---|---|---|
| NA-28[2] | 10.0 | 0.33 | 0.31 | N.R. |
| NA-34 | 7.2 | 2.00 | 0.48 | 27 |
| NA-35 | 6.4 | 1.99 | 0.48 | 35 |
| NA-37 | 33.2 | 0.68 | 0.28 | N.R. |
| NA-36[2] | 6.4[1] | 0.66 | 0.56 | N.R. |
| NA-38[2] | 6.4[1] | 0.49 | 0.49 | N.R. |

[1]The activity of the processing composition was increased by the addition of 10 g/l of benzyl alcohol.
[2]The image discrimination ($D_{max}$ minus $D_{min}$) was substantially increased in similarly prepared, exposed and processed photographic elements when the emulsion layer was coated at a pH in the range of from 4.8 to 5.0 instead of 6.0.
* N.R. = Not Recorded.

48. Comparison of multicolor photographic elements

A control integral multicolor photographic element, Element 4, was prepared by coating the following layers in the order given on a poly(ethylene terephthalate) film support (coverages in parenthesis in g/m² unless indicated):

1. image-receiving layer of a poly[styrene-co-N-benzyl-N,N-dimethyl-N-vinylbenzyl-co-divinylbenzene] latex (2.2) and gelatin (2.2).
2. reflecting layer of titanium dioxide (21.5) and gelatin (3.2).
3. opaque layer of carbon black (2.7) and gelatin (1.7).
4. cyan dye redox releaser Compound A (0.54) dispersed in gelatin (1.1).
5. interlayer of gelatin (0.54).
6. red-sensitive, direct-positive, internal image gelatin-silver bromide emulsion (1.2 Ag, 1.1 gelatin), 5-sec-octadecylhydroquinone-2-sulfonic acid (16 g/mole silver) and nucleating agent H-25 (300 mg/mole silver).
7. interlayer of gelatin (1.1) and 2,5-di-sec-dodecylhydroquinone (1.1).
8. magenta dye redox releaser Compound B[2] (0.54) in diethyllauramide (0.27) dispersed in gelatin (1.1).
9. green-sensitive, direct-positive, internal image gelatin-silver bromide emulsion (1.35 Ag, 100 gelatin), 5-sec-octadecylhydroquinone-2-sulfonic acid (16 g/mole Ag), and nucleating agent H-25 (400 mg/mole Ag).
10. interlayer of gelatin (1.2) and 2,5-di-sec-dodecylhydroquinone (1.1).
11. yellow dye redox releaser Compound C[3] (0.86) in diethyllauramide (0.43) dispersion gelatin (1.1).
12. blue-sensitive, direct-positive, internal-image gelatin-silver bromide emulsion (1.25 Ag, 1.1 gelatin), 5-sec-octadecyl-5-hydroquinone-2-sulfonic acid (16 g/mole Ag), and nucleating agent H-25 (500 g/mole Ag).
13. overcoat lyer of gelatin (0.54) and 2,5-di-sec-dodecylhydroquinone (0.11).

[2]Compound B

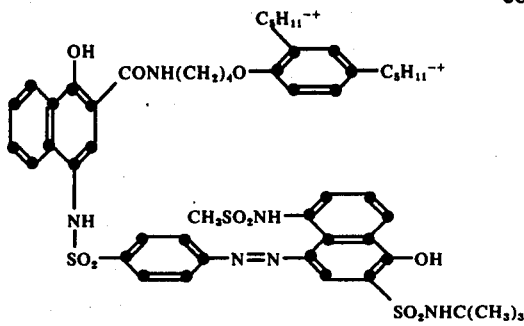

*Compound C

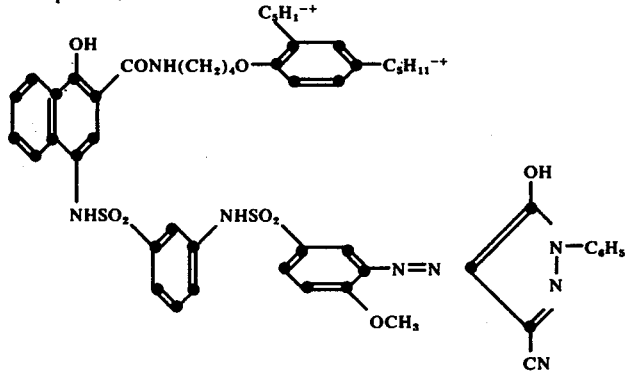

A series of analogous photographic elements, Elements 5 through 9, were prepared by substituting the acylhydrazinophenylthiourea fogging agents of the invention for nucleating agent H-25 in the emulsion layers 12 (blue-senstive), 9 (green-sensitive), and 6 (red-sensitive).

The above-prepared photosensitive elements were then exposed to a graduated density multicolor test object. The following processing composition was employed in a pod and was spread between duplicate samples of the photosensitive element and the transparent cover sheet described below — one at 15° C, the other at 38° C — by passing the transfer sandwich between a pair of juxtaposed rollers so that the liquid layer was about 70 microns in thickness.

The cover sheet was identical to that employed above (46. Comparison of single color photographic elements).

The processing composition was as follows:

| | |
|---|---|
| Potassium hydroxide | 56.0 G |
| 4-Hydroxymethyl-4-methyl-1- | |

-continued

| | |
|---|---|
| phenyl-3-pyrazolidone | 8.0 g |
| 5-Methylbenzotriazole | 2.4 g |
| T-Butylhydroquinone | 0.2 g |
| Sodium sulfite (anhyd) | 2.0 g |
| Carbon | 100.0 g |
| Carboxymethylcellulose | 51.0 g |
| Benzyl alcohol | 10.0 ml |
| Water to make | 1.0 liter. |

Table VI shows the maximum ($D_{max}$) and minimum ($D_{min}$) dye densities in the image-receiving layer as read by reflection densitometry through the film support of the laminate. The speed values were taken at a density of 0.7 on the reversal sensitometric curve.

The data show good image discrimination resulting from the action of the incorporated nucleating agents in the image-forming layers. Control nucleating agent H-25 showed substantial speed losses on high temperature (38° C) processing as compared to the low temperature (15° C) processing. The adsorbed hydrazine nucleating agents of the invention showed improved processing latitude both in regard to $D_{max}$ and speed changes.

TABLE VI

| Element | Fogging Agent | Nucleating Agent Concentration mg/mole Ag | | | $D_{max}$ at 15° C 38° C | | | $D_{min}$ at 15° C 38° C | | | Speed Change from 15° C to 38° C in log E | | |
|---|---|---|---|---|---|---|---|---|---|---|---|---|---|
| | | Blue | Green | Red | Blue | Green | Red | Blue | Green | Red | Blue | Green | Red |
| 4 | Control H-25 | 500 | 400 | 300 | 1.65 2.50 | 1.75 2.56 | 0.94 2.40 | 0.20 0.34 | 0.21 0.48 | 0.18 0.36 | −0.76 | −0.56 | −1.30 |
| 5 | NA-2 | 18 | 14 | 9 | 1.41 1.96 | 1.49 1.68 | 1.54 1.99 | 0.24 0.48 | 0.22 0.52 | 0.18 0.31 | −0.56 | −0.13 | +0.10 |
| 6 | NA-1 | 7 | 5 | 6 | 1.86 2.46 | 1.82 2.49 | 1.82 2.34 | 0.26 0.58 | 0.28 0.51 | 0.21 0.30 | −0.69 | −0.27 | +0.11 |
| 7 | NA-17 | 19 | 12 | 15 | 0.71 1.44 | 1.00 1.44 | 1.48 1.84 | 0.22 0.37 | 0.20 0.40 | 0.18 0.30 | low $D_{max}$ | −0.51 | −0.04 |
| 8 | NA-16 | 10 | 6 | 11 | 1.50 1.87 | 1.37 1.50 | 1.56 1.70 | 0.22 0.33 | 0.21 0.30 | 0.18 0.26 | −0.20 | +0.08 | +0.48 |
| 9 | NA-6 | 13 | 11 | 19 | 1.10 1.76 | 1.24 1.78 | 1.52 2.10 | 0.22 0.34 | 0.22 0.41 | 0.19 0.44 | −0.60 | −0.48 | −0.28 |

Some of the hydrazides surprisingly showed an increase in speed on high temperature processing, especially in the red-sensitive layer.

49. Nucleating agent combinations

An integral multicolor photographic element, Element 10, was coated similarly as Elements 4 through 9, except that a combination of nucleating agents were used in the green- and red-sensitive layers. The red-sensitive layer (6) contained (each in mg/mole of silver) H-25 (150) and NA-16 (6.4). The green-sensitive layer (9) contained compound H-25 (240) and NA-16 (4.8). The blue-sensitive layer 12 contained only the nucleating agent NA-16 (11.0)

The element was exposed to a tungsten light through a graduated density multicolor test object having 0.15 log E steps and processed using a cover sheet as described in connection with Elements 4 through 9 at 15°, 24°, and 38° C. The processing composition was formulated as follows:

| | |
|---|---|
| Potassium hydroxide | 56.0 g |
| 4-Hydroxymethyl-4-methyl-1-phenyl-3-pyrazolidone | 8.0 g |
| 5-Methylbenzotriazole | 2.4 g |
| t-Butylhydroquinone | 0.2 g |
| Sodium sulfite | 10.0 g |
| Carboxymethylcellulose | 51.0 g |
| Carbon | 100.0 g |
| 1,4-Cyclohexanedimethanol | 10.0 g |
| Water | 1000.0 g |

The sensitometric curves were obtained by color reflection densitometry at least three hours after lamination. Representative densities and relative speeds (read at a density of 1.0) are given in the following table: Step 14 is the fourteenth density step in the above test object, wherein the test object has 21 density steps and Step 1 permits maximum exposure.

TABLE VII

| | | | Development Temperature ° C | | |
|---|---|---|---|---|---|
| | | | 15° | 24° | 38° |
| Density | Red | $D_{min}$ | 0.22 | 0.23 | 0.56 |
| | | Step 14 | 1.08 | 1.22 | 1.72 |
| | | $D_{max}$ | 1.66 | 1.92 | 2.28 |
| | Green | $D_{min}$ | 0.21 | 0.24 | 0.52 |
| | | Step 14 | 1.12 | 1.12 | 1.41 |
| | | $D_{max}$ | 1.72 | 1.85 | 2.16 |
| | Blue | $D_{min}$ | 0.26 | 0.27 | 0.45 |
| | | Step 14 | 0.91 | 0.91 | 1.26 |
| | | $D_{max}$ | 1.66 | 1.74 | 2.06 |
| Relative Speed | Red | | 100 | 91 | 51 |
| | Green | | 100 | 100 | 66 |
| | Blue | | 129 | 129 | 85 |

The data show that by adjusting the level of nucleating agents that the sensitometry of each layer can be stabilized over the temperature range of 15° to 24° C with the speed change on 38° C over-development beng about the same for each layer (loss of less than one camera stop).

The invention has been described with particular reference to preferred embodiments thereof, but it will be understood that variations and modifications can be effected within the spirit and scope of the invention.

We claim:

1. A compound having the formula

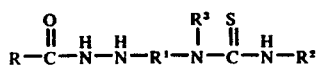

wherein
R is a hydrogen, phenyl, alkylphenyl, cyanophenyl, halophenyl, alkoxyphenyl, alkyl, cycloalkyl, haloalkyl, alkoxyalkyl or phenylalkyl substituent;
$R^1$ is a phenylene or alkyl, halo- or alkoxy substituted phenylene;
$R^2$ is an alkyl, haloalkyl, alkoxyalkyl or phenylalkyl substituent having up to 18 carbon atoms; a cycloalkyl substituent; phenyl or naphthyl; an alkylphenyl, cyanophenyl, halophenyl or alkoxyphenyl substituent or

$R^3$ is hydrogen, benzyl, alkoxybenzyl, halobenzyl or alkylbenzyl;
said alkyl moieties, except as otherwise noted, in each instance include from 1 to 6 carbon atoms; and
said cycloalkyl moieties have from 3 to 10 carbon atoms.

2. A compound according to claim 1 wherein said alkyl moieties of R consist of from 1 to 4 carbon atoms.

3. A compound according to claim 1 wherein $R^1$ is a para-phenylene group.

4. A compound of the formula:

wherein
R is a hydrogen, phenyl, alkylphenyl, cyanophenyl, halophenyl, alkoxyphenyl, alkyl, cycloalkyl, haloalkyl, alkoxyalkyl or phenylalkyl substituent;
$R^1$ is a phenylene or alkyl, halo- or alkoxy substituted phenylene;
$R^2$ is an alkyl, haloalkyl, alkoxyalkyl or phenylalkyl substituent having up to 18 carbon atoms; a cycloalkyl substituent; phenyl or naphthyl; or an alkylphenyl, cyanophenyl, halophenyl or alkoxyphenyl substituent;
$R^3$ is benzyl, alkoxybenzyl, halobenzyl or alkylbenzyl;
said alkyl moieties, except as otherwise noted, in each instance include from 1 to 6 carbon atoms; and
said cycloalkyl moieties have from 3 to 10 carbon atoms.

5. A compound according to claim 4 wherein said alkyl moieties of R consist of from 1 to 4 carbon atoms.

6. A compound according to claim 4 wherein $R^2$ is an alkyl substituent having from 1 to 12 carbon atoms; a cyclohexyl substituent; phenyl; or 4-alkylphenyl, 4-halophenyl or 4-alkoxyphenyl substituent.

7. A compound according to claim 4 wherein $R^1$ is a para-phenylene.

8. 1-[4-(2-Acetylhydrazino)phenyl]-1-benzyl-3-phenylthiourea.

9. 1-[4-(2-Acetylhydrazino)phenyl]-1-(4-methoxybenzyl)-3-phenylthiourea.

10. A compound having the formula

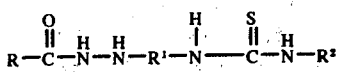

wherein
R is a hydrogen, phenyl, alkylphenyl, cyanophenyl, halophenyl, alkoxyphenyl, alkyl, cycloalkyl, haloalkyl, alkoxyalkyl or phenylalkyl substituent;
R¹ is a phenylene or alkyl, halo- or alkoxy substituted phenylene group;
R² is an alkyl, haloalkyl, alkoxyalkyl or phenylalkyl substituent having up to 18 carbon atoms; a cycloalkyl substituent; phenyl or naphthyl; an alkylphenyl, cyanophenyl, halophenyl or alkoxyphenyl substituent or

said alkyl moieties, except as otherwise noted, in each instance include from 1 to 6 carbon atoms; and said cycloalkyl moieties have from 3 to 10 carbon atoms.

11. A compound according to claim 10 wherein said alkyl moieties of R consist of from 1 to 4 carbon atoms.

12. A compound according to claim 10 wherein R² is an alkyl substituent having from 1 to 12 carbon atoms; a cyclohexyl substituent; phenyl; or a 4-alkylphenyl, 4-halophenyl or 4-alkoxyphenyl substituent.

13. A compound according to claim 10 wherein R¹ is a para-phenylene or para-phenylene substituted in the 3 position with an alkyl, halo- or alkoxy substituent.

14. A compound having the formula

wherein
R is a hydrogen, phenyl, 4-alkylphenyl, 4-halophenyl, 4-alkoxyphenyl, alkyl, cyclohexyl or phenylalkyl substituent; wherein said alkyl moieties have from 1 to 4 carbon atoms;
R¹ is a para-phenylene or a 3 position alkyl, halo- or alkoxy substituted para-phenyene group; and
R² is an alkyl, haloalkyl, alkoxyalkyl or phenylalkyl substituent having up to 2 carbon atoms; a cyclohexyl substituent; phenyl; or a 4-alkylphenyl, 4-halophenyl or 4-alkoxyphenyl substituent; wherein said alkyl moieties, except as otherwise noted, in each instance include from 1 to 6 carbon atoms.

15. 1-[4-(2-Formylhydrazino)phenyl]-3-phenylthiourea.
16. 1-[4-(2-Acetylhydrazino)phenyl]-3-phenylthiourea.
17. 1-[4-(2-Benzoylhydrazino)phenyl]-3-phenylthiourea.
18. 1-[4-(2-Formylhydrazino)phenyl]-3-methylthiourea.
19. 1-[4-(2-Acetylhydrazino)phenyl]-3-ethylthiourea.
20. 1-[4-(2-Formylhydrazino)phenyl]-3-butylthiourea.
21. 1-[4-(2-Formylhydrazino)phenyl]-3-cyclohexylthiourea.
22. 1-[4-(2-Formylhydrazino)phenyl]-3-benzylthiourea.
23. 1-[4-(2-Formylhydrazino)phenyl]-3-heptylthiourea.
24. 1-[4-(2-Formylhydrazino)phenyl]-3-decylthiourea.
25. 1-[4-(2-Formylhydrazino)phenyl]-3-(4-cyanophenyl)thiourea.
26. 1-[4-(2-Formylhydrazino)phenyl]-3-(4-methoxyphenyl)thiourea.
27. 1-[4-(2-Formylhydrazino)-3-methoxyphenyl]-3-phenylthiourea.
28. 1-[4-(2-Formylhydrazino)-3-methoxyphenyl]-3-butylthiourea.
29. 1-[4-(2-Formylhydrazino)-3-methoxyphenyl]-3-cyclohexylthiourea.
30. 1-[4-(2-Formylhydrazino)-3-methoxyphenyl]-3-(4-methoxyphenyl)thiourea.
31. 1-[4-(2-Trifluoroacetylhydrazino)phenyl]-3-phenylthiourea.
32. 1-{4-[2-(4-Cyanobenzoyl)hydrazino]phenyl}-3-phenylthiourea.
33. 1-{-4-[2-(4-Chlorobenzoyl)hydrazino]phenyl}-3-phenylthiourea.
34. 1-{4-[2-(4-Flourobenzoyl)hydrazino]phenyl}-3-phenylthiourea.
35. 1-{4-[2-(4-Methylbenzoyl)hydrazino]phenyl}-3-phenylthiourea.
36. 1-{4-[2-(4-Methoxybenzoyl)hydrazino]-phenyl}-3-phenylthiourea.
37. 1-{4-[2-(4-Chlorobenzoyl)hydrazino]phenyl}-3-benzylthiourea.
38. 1-{4-[2-(4-Flourobenzoyl)Hydrazino}-3-benzylthiourea.
39. 1-[3-(2-Formylhydrazino)phenyl]-3-phenylthiourea.
40. 1-[3-(2-Formylhydrazino)phenyl]-3-(4-methoxyphenyl)thiourea.
41. 1-[2-(2-Formylhydrazino)phenyl]-3-phenylthiourea.
42. A compound having the formula

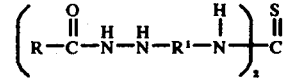

wherein
R is a hydrogen, phenyl, 4-alkylphenyl, 4-halophenyl, 4-alkoxyphenyl, alkyl, cyclohexyl or phenylalkyl substituent;
R¹ is para-phenylene or a 3-position alkyl, halo- or alkoxy substituted para-phenylene group; and
said alkyl moieties in each instance include from 1 to 4 carbon atoms.

43. 1,3-Bis[4-(2-formylhydrazino)phenyl]thiourea.
44. 1,3-Bis[4-(2-acetylhydrazino)phenyl]thiourea.
45. 1,3-Bis[4-82-benzoylhydrazino)phenyl]thiourea.

* * * * *

UNITED STATES PATENT AND TRADEMARK OFFICE
CERTIFICATE OF CORRECTION

PATENT NO. : 4,031,127

DATED : June 21, 1977

INVENTOR(S) : Leone et al

It is certified that error appears in the above-identified patent and that said Letters Patent are hereby corrected as shown below:

Title page, item [75], after "Weber", "," should be deleted; item [56], line 3, "260/552 R X" should read --260/552.R(XR)--; item [56], line 6, "96/64 X" should read --96/64(XR)--. Column 1, line 50, "image-wise" should read --imagewise--; line 55, "imae" should read --image--. Column 3, line 53, before the formula, --(I)-- should be inserted. Column 4, line 48, "moeity" should read --moiety--. Column 5, line 66, "chilld" should read --chilled--. Column 7, line 49, "techniqiues" should read --techniques--. Column 8, line 41, "Davel" should read --Davey--. Column 11, line 35, "3,220,884" should read --3,220,844--. Column 12, line 57, "PS" should be deleted. Column 14, line 4, that part of the formula reading "benzamido)2,5" should read --benzamido)-2,5--. Column 15, line 33, that part of the formula reading "1,3-dioxolan-2yl)" should read --(1,3-dioxolan-2-yl)--. Column 16, line 44, "perferably" should read --preferably--. Column 18, line 1, before "means", --3.-- should be inserted at the left margin of the column; "means" should be moved flush with the word "adapted" (on the second line);

Column 19, line 41, "fumaric" should read --formic--. Column 24, line 19, that part of the formula reading "phenyl[" should read --phenyl]--. Column 26, line 60, "or" should read --on--. Column 27, line 1, that part of the formula reading "1- 4"

UNITED STATES PATENT AND TRADEMARK OFFICE
CERTIFICATE OF CORRECTION

PATENT NO. : 4,031,127

DATED : June 21, 1977

INVENTOR(S) : Leone et al

It is certified that error appears in the above-identified patent and that said Letters Patent are hereby corrected as shown below:

should read --1-{4--; line 1, that part of the formula reading "phenyl -3" should read --phenyl}-3--; line 19, "0.1" should read --0.01--; line 27, that part of the formula reading "1 -4" should read --1-{4--; line 27, that part of the formula reading "phenyl -3" should read --phenyl}-3--; lines 31-37, there is no indication in the printed patent that the two lines are one continuous formula; line 44, that part of the formula reading "1-X--" should read --1-{2--; line 45, that part of the formula reading "phenyl -3" should read --phenyl}-3--; line 62, that part of the formula reading "1- 4" should read --1-{4--; line 62, that part of the formula reading "phenyl -3" should read --phenyl}-3--. Column 28, line 14, that part of the formula reading "1- 4" should read --1-{4--; line 14, that part of the formula reading "phenyl -3" should read --phenyl}-3--; line 32, that part of the formula reading "1- 4" should read --1-{4--; lines 32-33, that part of the formula reading "phenyl-thiourea" should read --phenyl}thiourea--; line 58, that part of the formula reading "1- 4" should read --1-{4--; lines 58-59, that part of the formula reading "phenyl-thiourea" should read --phenyl}thiourea--. Column 29, line 2, that part of the formula reading "2-(4-fluorobenzoyl-" should be deleted; line 9, that part of the formula reading "(3-" should be deleted. Column 32, line 32, "(16:1)" should read --(16.1)--; line 57, "emulsions" should read --emulsion--. Column 33, line 11, "coacrylic" should read --co-acrylic--. Column 34, line 57, "lyer" should read --layer--; last line, "²Compound B" should be located at the head of col-

UNITED STATES PATENT AND TRADEMARK OFFICE
CERTIFICATE OF CORRECTION

PATENT NO. : 4,031,127

DATED : June 21, 1977

INVENTOR(S) : Leone et al

It is certified that error appears in the above-identified patent and that said Letters Patent are hereby corrected as shown below:

umn 35 in front of the formula to which it pertains. Column 35, second formula, that part of the formula reading "$C_5H_1-t$" should read --$C_5H_{11}-t$--; line 34, "(blue-senstive)" should read --(blue-sensitive)--; line 42, "sandwich" should read --"sandwich"--. Column 37, line 57, "beng" should read --being--. Column 39, line 47, "para-phenyene" should read --para-phenylene--. Column 40, line 30, that part of the formula reading "Flourobenzoyl" should read --Fluorobenzoyl--; line 38, that part of the formula reading "Flourobenzoyl)Hydrazino]"should read --Fluorobenzoyl)hydrazino]phenyl}--; last line, that part of the formula reading "82" should read --(2--.

Signed and Sealed this

Thirteenth Day of June 1978

[SEAL]

Attest:

RUTH C. MASON
*Attesting Officer*

DONALD W. BANNER
*Commissioner of Patents and Trademarks*